(12) United States Patent
Schultze et al.

(10) Patent No.: US 6,465,251 B1
(45) Date of Patent: *Oct. 15, 2002

(54) METHOD OF PROMOTING B-CELL PROLIFERATION AND ACTIVATION WITH CD40 LIGAND AND CYCLOSPORIN

(75) Inventors: Joachim L. Schultze; Gordon J. Freeman; John G. Gribben, all of Brookline; Lee M. Nadler, Newton, all of MA (US)

(73) Assignee: Dana-Farber Cancer Institute, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/748,341

(22) Filed: Nov. 13, 1996

(51) Int. Cl.⁷ .............................. C12N 5/02; C12N 5/06; C12N 5/08; C12N 5/12
(52) U.S. Cl. ........................... 435/377; 435/2; 435/325; 435/326; 435/352; 435/355; 435/363; 435/366; 435/372; 435/372.1; 435/372.2; 435/374; 435/375; 435/376; 435/383
(58) Field of Search .............................. 424/93.7; 435/2, 435/325, 326, 352, 355, 363, 366, 372, 372.1, 372.2, 374, 375, 376, 377, 383

(56) References Cited

U.S. PATENT DOCUMENTS 5,283,323 A * 2/1994 Berzofsky et al.

FOREIGN PATENT DOCUMENTS

| EP | 0434879 A1 | * 7/1991 |
| WO | WO 94/20127 | 9/1994 |
| WO | WO 95/29935 | 11/1995 |

OTHER PUBLICATIONS

Fuleihan et al. J Clin Invest. 93: 1315–1320 (1994).*
Chang et al. Ann NY Acad Sci 696: 108–122 (1993).*
Wortis et al. PNAS 92: 3348–3352 (1995).*
Khaukin et al. Abstr Annu Meeting Am Soc Microbiol. 90(0):333 (1990).*
Banchereau et al. Ann Rev Immunol. 12: 881–892 (1994).*
Kim et al. Clin Exp. Immunol. 96:508–512 (1994).*
Freeman, G.J., et al., *Science* 262:909–911(1993).
Grabbe, S., et al., *Immunol Today* 16:117–121 (1995).
Inaba, K., et al., *J Exp Med* 166:182–194 (1987).
June, C.H., et al., *Immunol. Today* 11:211–216 (1990).
June, C.H., et al., *Immunol Methods* 164:41–49 (1994).
Linsley, P.S., et al., *J Exp Med* 173:721–730 (1991).
Mackensen, A., et al., *Blood* 86:2699–2707 (1995).
Nussenzweig, M.C., et al., *J Exp Med* 151:1196 (1980).
Paglia, P., et al., *J Exp Med* 183:317–322 (1996).
Romani, N., et al., *J Exp Med* 180:83–93 (1994).
Schwartz, R.H., *Cold Spring Harb Symp Quant Biol* 54:605–610 (1989).
Schwartz, R.H., et al., *Cell* 71:1065–1068.
Steinman, R.M., et al., *Annual Review of Immunology* 9:271–296 (1991).
Steinman, H.M., et al., *Current Opinion in Immunology* 3:361–372 (1991).
Szabolcs, P., et al., *J Immunol* 154:5851–5861 (1995).
Tew, J.G., et al., *J Reticuloendothel Soc* 31:371 (1982).
Young, J.W., et al., *J Exp Med* 183:7–11 (1996).
Zitvogel, L., et al., *J Exp Med* 183:87–97 (1996).
J. Schultze et al., *Blood,* vol. 88, No. 10, Suppl. part 1–2, pp. 6–10 (1996).
J. Schultze et al., *Journal of Clinical Investigation,* 100(11):2757–2565 (1997).
J. Banchereau et al., *Science,* 251(4989):70–72 (1991).
J. Banchereau et al., *Nature,* 353(6345):678–679 (1991).

* cited by examiner

*Primary Examiner*—Phillip Gambel
(74) *Attorney, Agent, or Firm*—Nixon & Peabody LLP

(57) ABSTRACT

We teach a strategy to obtain large quantities of desired APCs, activated B cells, which are superior in their capacity to present tumor protein antigen in a multiadministration protocol. Human B cells can be obtained from peripheral blood in large numbers. These cells can be activated in vitro by coculture with CD40L (CD40-B cells) and an immunosuppressive agent such as cyclosporin A. They can expanded up to $1 \times 10^3$ to $1 \times 10^4$ fold in 2 weeks or $1 \times 10^5$ to $1 \times 10^6$ fold in 2 months. We demonstrate these cells are most efficient APCs comparable to DCs in stimulating allogeneic $CD4^+$ $CD45RA^+$, $CD4^+$ $CD45RO^+$, and $CD8^+$ T cells. In contrast to DCs, CD40-B cells are fully functional even in the presence of immunosuppressive cytokines such as IL-10 and TGFβ.

11 Claims, 8 Drawing Sheets

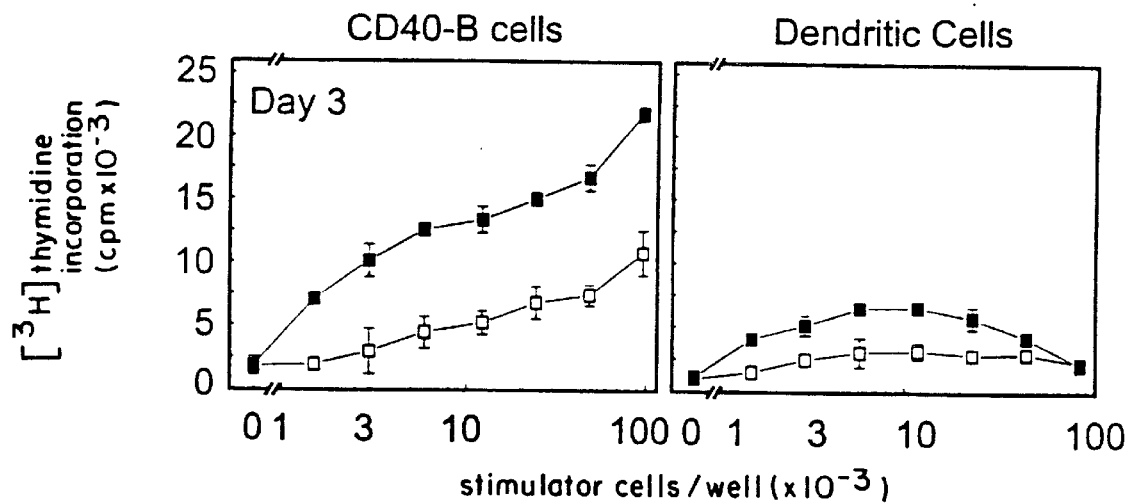
F I G. 2A
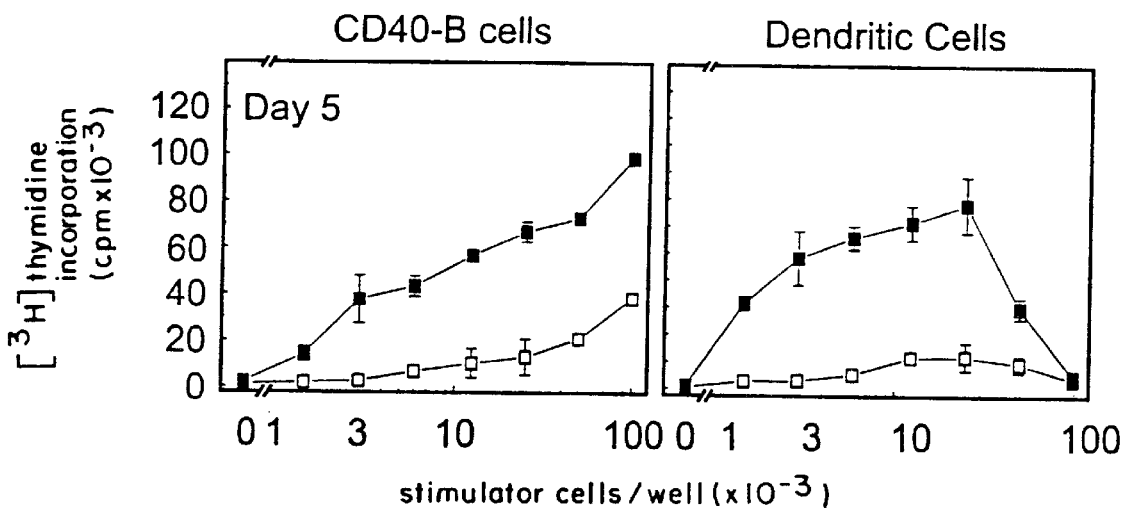
F I G. 2B
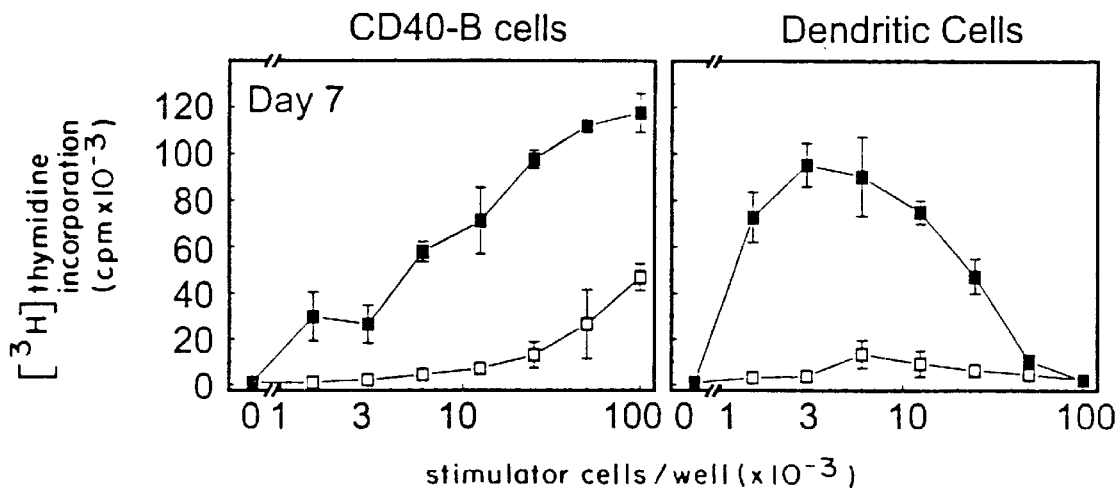
F I G. 2C

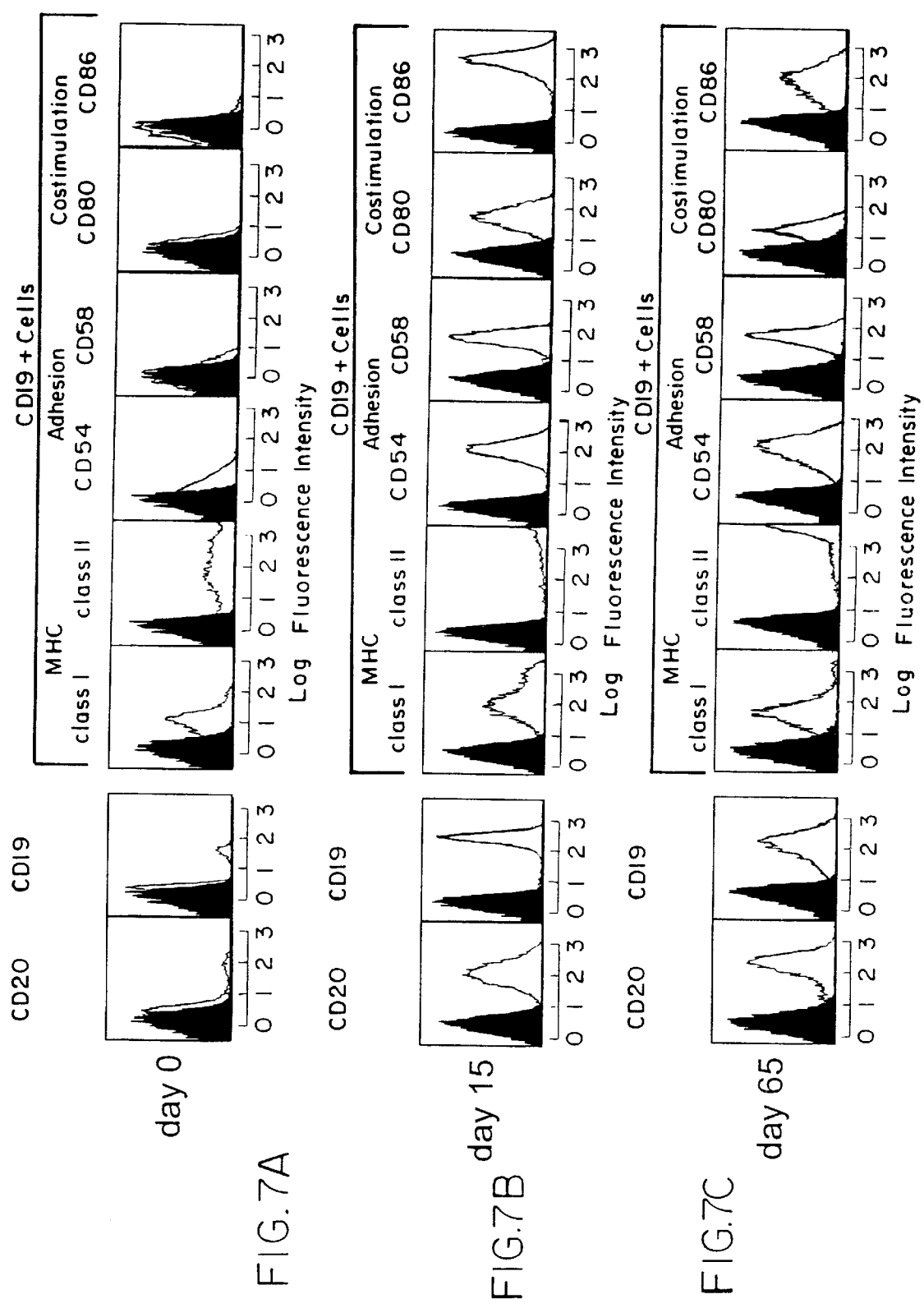
FIG. 7A  day 0
FIG. 7B  day 15
FIG. 7C  day 65

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: linear (xi) SEQUENCE DESCRIPTION: SEQ ID NO:1:

Tyr Met Asn Gly Thr Met Ser Gln Val
1             5

(2) INFORMATION FOR SEQ ID NO:2:

(i) SEQUENCE CHARACTERISTICS:
      (A) LENGTH: 9 amino acids
      (B) TYPE: amino acid

```
            (C) STRANDEDNESS: single
            (D) TOPOLOGY: linear (xi) SEQUENCE DESCRIPTION: SEQ ID NO:2:

Gly Ile Leu Gly Phe Val Phe Thr Leu
 1               5
```

METHOD OF PROMOTING B-CELL PROLIFERATION AND ACTIVATION WITH CD40 LIGAND AND CYCLOSPORIN

This invention was made in the course of research funded in part by the U.S. Government under NIH Grants CA 34183, AI 35225 and CA 40216. Therefore, the U.S. Government has certain rights in the invention.

The present invention relates to a novel method of administration of antigen presenting cells during a multi-administration immune generation protocol. In one embodiment it relates to a novel method of obtaining large quantities of a preferred class of antigen presenting cells, activated B cells.

BACKGROUND

The traditional approach to generating an immune response was based upon an antigen-antibody reaction, for example by administration of an inactive whole virus. However, our understanding of generating immune responses has increased significantly in recent years. Thus, attention has expanded beyond simply presenting such an antigen. It was recognized that T cells interact most effectively with cells having major histocompatibility complexes (MHC) associated antigens and not soluble antigens. There are two different types of MHC-associated antigens, namely class I and class II. The antigens associated with a particular class of MHC molecule determines the kinds of T cells stimulated by the molecule. Typically, peptide fragments derived from extracellular proteins bind to class II molecules, whereas endogenously synthesized peptides associate with class I molecules.

There are many areas where the traditional presentation of an antigen has not, thus far, generally proven clinically successful such as using tumor-associated antigens, HIV, etc. Thus, considerable attention has focused on understanding the method of generating and regulating immune reactions such as those generated by the MHC-antigens, in order to more appropriately regulate the process.

It was discovered that there is a group of cells that typically process proteins via endocytosis thereby subjecting them to enzymatic and chemical degradation to result in a "processed" peptide. This peptide will then bind to an MHC molecule which transports it to the surface where it is presented a to T cells for appropriate interaction. Such cells are called antigen presenting cells (APCs). Thus, paradigms have been proposed for the appropriate structure of MHC I and MHC II peptides that are presented. [WO 94/20127; Bartholomew, J. S., et al., Eur. J. Immunol. 24:3175–3179 (1994); Falk, K., et al., Nature 351: 290–296 (1991)]. For example, MHC class I molecules bind preferentially to peptides 8–10 residues, whereas class II molecules bind preferentially to peptides 12–25 residues long. In these peptides, there are certain amino acid residues that are more critical and tolerate only certain amino acids. Similarly, there are limitations on the cells that can serve as APCs for one class of molecules as opposed to another. The number of cells that are suitable class II APCs is substantially smaller than for class I. It would be desirable to have an APC that will be useful with both MHC classes. Although it has been known that a number of different cells naturally can be used as MHC class II APCs, such as mononuclear phagocytes, dendritic cells (DCs), Langerhans cells of the skin, activated B lymphocytes and endothelial cells, considerable attention has focused on using dendritic cells as the APC. The reason for this attention includes its high efficiency in antigen presentation, relative ease of isolation [Mackensen 1995 #56] and relative ease of culturing. For example, DCs are about 5–10 fold more efficient at presenting alloAg than activated B cells. DC can be obtained as stem cell derived DCs, either from bone marrow or peripheral blood stem cells, or peripheral blood derived DCs. Dendritic cells prepared from bone marrow cells [Caux, 1992 #55]; Mackensen, 1995 #56; Szabolcs, 1995 #73; Bernhard, 1995 #74], demonstrate APC function [Nussenzweig, 1980 #12; Tew, 1982 #58; Steinman, 1991 #64; Steinman, 1991 #65], and the knowledge of definition of the culture conditions needed to expand larger numbers of dendritic cells [Mackensen, 1995 #56]; Inaba, 1992 #72] has made this cell population the present choice for use in vaccination strategies [Grabbe, 1995 #48]; Caux, 1995 #49; Young, 1996 #54]. Moreover, it was demonstrated in murine model systems that DCs pulsed with tumor peptide antigens in vitro can induce a T cell mediated tumor specific immune response in vivo [Paglia, 1996 #25]; Cohen, 1994 #51; Zitvogel, 1996 #50; Celluzzi, 1996 #52; Flamand, 1994 #53].

However, these cells have limitations, including diminished long term capacity. Stem cell derived DCs have to be expanded using several different cytokine cocktails. This procedure takes a relatively long time and is cost intensive. A culture period of 35 days under optimized conditions using 7 different cytokines was necessary to obtain $1.7 \times 10^7$ DCs from a starting population of $1 \times 10^6$ mononuclear cells of a peripheral stem cell (PBSC) preparation [Mackensen, 1995 #56]. In another study, to generate DCs in vitro from peripheral blood high amounts of GM-CSF and IL-4 were necessary [Romani, 1994 #14]. The yield of DC in that study was about $3–8 \times 10^7$ DCs from 40–100 ml peripheral blood after 5–8 days of culture, but growth ceased at that time and no further expansion was possible. Another limitation of generating DCs from bone marrow (BM) or peripheral blood (PB) is the decreased ability of long term cultured cells to function as APC [Mackensen, 1995 #56] due to down-regulation of important molecules such as CD80 (B7-1). Yet, another limitation is that DCs cannot be stored long term since they cannot be cryogenically frozen.

It would be desirable to be able to use other cells as APCs, if they could be prepared more efficiently and effectively then dendritic cells.

Typical modes of generating immune reaction involve multiple injections of APCs over a course of administration that takes place over extended periods of time. General protocols require an initial administration and subsequent boosts at intervals ranging from one to two weeks to up to several months. One preferred protocol is to administer the APCs approximately at 1 to 2 weeks intervals, 5 to 10 times, more preferably 6–7 times. However, such protocols effectively limit the use of one draw of dendritic cells to at most 2 administrations before additional blood must be drawn, purified and cultured. Thus, in addition to receiving the boost, a patient will also have about 40–100 cc of blood drawn at each administration, in order to culture and prepare more DC.

It is now well established, that T cells are activated upon recognition of peptide antigen presented by the major histocompatibility complex (MHC) on professional antigen presenting cells (APCs) (signal 1) [Schwartz, 1989 #31; Schwartz, 1990 #32] in combination with costimulation which is mainly provided by members of the B7 family (signal 2), on the APC to the CD28 molecule on the T cells [June, 1990 #29; June, 1994 #30]; Schwartz, 1992 #33; Linsley, 1991 #34; Freeman, 1989 #35; Freeman, 1993 #36].

White dendritic cells, B cells and macrophages are known to function as APCs. However, it is still not clear whether all APCs function in concert during (1) onset, (2) amplification and (3) expansion of an immune response or whether there is a hierarchy of interactions between professional APCs and T cells. In addition, different routes of entry of antigens into the organism and their different origin might influence which APC might play the major role in an immune response. Consequently, being able to use different APCs would be desirable. However, heretofore, when multiple administrations were necessary, the use of DCs was preferable to the use of activated B cells because one would have to administer a greater number of activated B cells then DCs to obtain the same effect. Although B cells are known to proliferate for long periods of time, they are typically outgrown by T cells. Even if one highly purified B cells, one could not get rid of all T cells present. Consequently, in a relatively short period of time, for example, 14 days, a considerable T cell population would be present in the B cell culture rapidly becoming the predominant population. Accordingly, it has not been feasible to use a single culture of B cells for a series of immunizations where multiple administrations were necessary.

We have now discovered a means that permits both the rapid proliferation of activated B cells, their purification from T cells, and their sustained culture thereby permitting the use of a single culture of B cells as the APCs in a multiple administration method of generating an immune response.

SUMMARY OF INVENTION

We have now discovered that activated B cells can be used to efficiently induce a T cell mediated immune response, thereby modulating an immune response in a multi-administration protocol. Preferably, the B cells help generate an immune response. As a result of our invention the activated B cells fulfill the following criteria: (1) they serve as APCs expressing all necessary molecules for antigen processing and presentation, (2) they are easily accessible, (3) they are expandable in vitro, and (4) they are able to present efficiently a desired peptide, such as a tumor antigen, to T cells. B cells express MHC class I and II and can therefore be used with a wide range of antigens.

While B cells are easily accessible from peripheral blood they have not previously met the criteria for use in the method proposed. Under physiological conditions resting B cells do not express all necessary molecules, such as the costimulatory molecules, to induce a sufficient T cell response [Jenkins, 1990 #37]. Instead, they were shown to anergize T cells [Matzinger, 1994 #38]; Fuchs, 1992 #39; Lassila, 1988 #41]. Only activated B cells express sufficient levels of costimulatory and adhesion molecules to induce T cell proliferation optimally [Schultze, 1995 #28; Boussiotis, 1993 #42]. The major B cell activation pathway is crosslinking of CD40 by CD40L (sometimes also referred to as gp39) that is expressed on activated T cells [Banchereau, 1994 #43]; Armitage, 1992 #44; Clark, 1994 #6064; Hollenbaugh, 1992 #45; Hollenbaugh, 1994 #46]. Normal and malignant B cells can be activated in vitro with transfectants expressing the CD40L. Once activated these CD40-activated B cells (CD40-B) express high levels of MHC molecules as well as adhesion and costimulatory molecules [Schultze, 1995 #281; Ranheim, 1993 #47]. The activated cells are highly efficient antigen presenting cells [Schultze, 1995 #28], and the B cells can be expanded in this culture system [Banchereau, 1994 #43]. However, the methods used to activate B cells also activated T cells. B cells constitute a very small percentage of blood and are difficult, if not impossible, to purify so that no T cells are present. Since, the co-cultured T cells outgrow the B cells, the T cells rapidly become the predominant species being cultured.

We have overcome the problem and discovered a method where normal human B cells can be obtained easily from peripheral blood, do not need to be enriched prior to culture, can be expanded in vitro with a CD40L, e.g., on CD40L transfectants, express all necessary molecules for antigen presentation, and induce proliferation of allogeneic $CD4^+$ and $CD8^+$ T cells. This method involves using an immune suppressor under conditions where it preferentially affects T cells, rather than B cells. Thus, the use of compounds such as cyclosporin A (sometimes also called cyclosporine), mycophenolate mofetil, azathioprine and tacrolimus. More preferably, cyclosporin A. As a result of this method, one can obtain an activated B cell culture that is highly purified. Preferably, at least 85% pure, still more preferably at least 90% pure, even more preferably at least 98% pure and most preferably at least 99% pure.

The cultures can be grown over long periods of time—with increasing activated B cell number. Preferably, at least 2 months, more preferably at least 3 months, still more preferably at least 6 months.

Additionally, the activated B cells can be cryopreserved. Cryopreserved material can be used even 5 years later.

The activated B cells can thus be used as APCs from a single culture over an extended period of time. One can combine the APC with a desired antigen or a cocktail of antigens by a variety of techniques well known in the art. For example, one can present the whole antigen, which is then processed, a specific peptide, nucleic acid encoding the antigen or the peptide. One preferred method is to target a nucleic acid encoding a desired antigen to a particular cellular compartment. Another embodiment involves culturing the APC with the protein or peptide (pulsing) for a sufficient time for the APC to process and present the MHC-bound peptide. Thereafter one administers the active APC to the subject. The magnitude of T cell proliferation is dependent on cell number of APCs administered. Because of the large cell number that can be obtained over time the T-cell reaction can be greater than that induced by DCs. Any appopriate desired target antigen can be used. For example, we have shown that our CD40-B cells can be pulsed with tumor peptide to induce autologous $CD8^+$ T cells to proliferate and kill target cells expressing the antigen. Additionally, the T cell proliferation induced by DCs in the presence of immunosuppressive cytokines is significantly diminished. In contrast, when our CD40-B cells were used under such conditions there was not a reduction in activity.

BRIEF DESCRIPTION OF THE DRAWINGS

FIG. 1A shows lineage marker analysis. FIG. 1B shows molecules necessary for APC function. Cells were stained with directly conjugated mAb. Black shaded area indicates fluorescence of isotype matched conjugated Ab.

FIGS. 2A–2C show response of allogeneic $CD3^+$ $CD4^+$ $CD45RO^+$ T cells to purified CD40-B cells or DC at 3 days (FIG. 2A), 5 days (FIG. 2B) or 7 days (FIG. 2C). Purified T cells were co-cultured with CD40-activated (CD40-B) B cells or DC generated from peripheral blood. [$^3$H] Thymidine incorporation was assessed for the last 16 hr of a 3-, 5- or 7-day culture. Appropriate controls ($CD3^+$ $CD4^+$ $CD45RO^+$ T cells, stimulator cells) were always <2000 cpm.

The ability of purified T cells (from other normal donors with unrelated MHC) to proliferate in response to CD40-B cells or DC was tested in a total of 5 experiments.

Figure 3A:
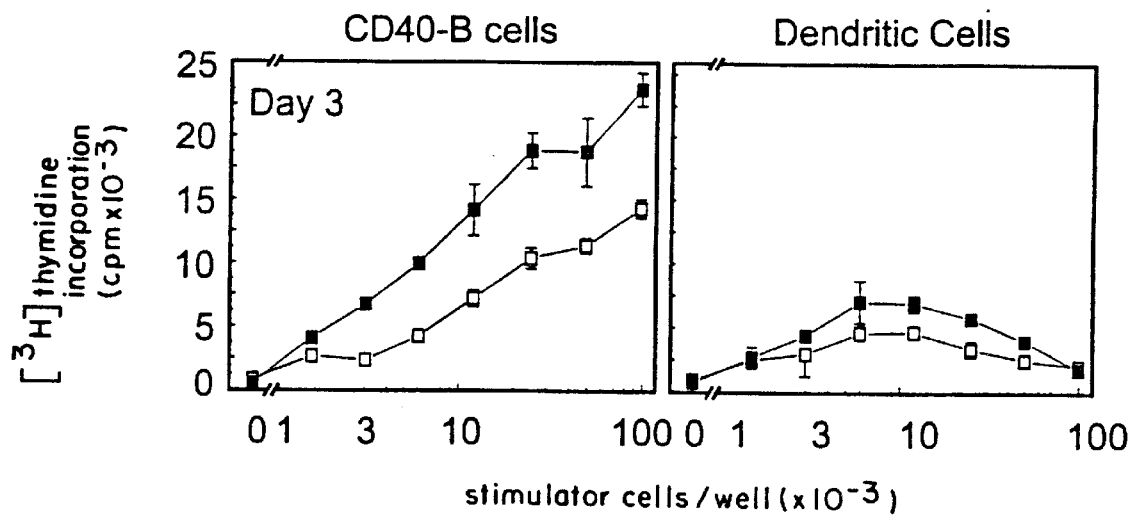
Figure 3B:
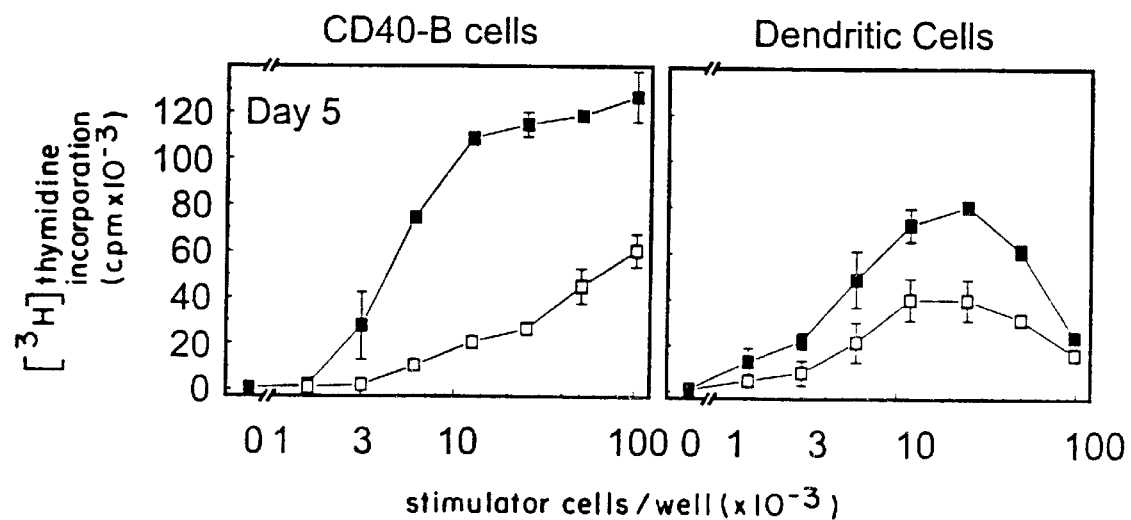
Figure 3C:
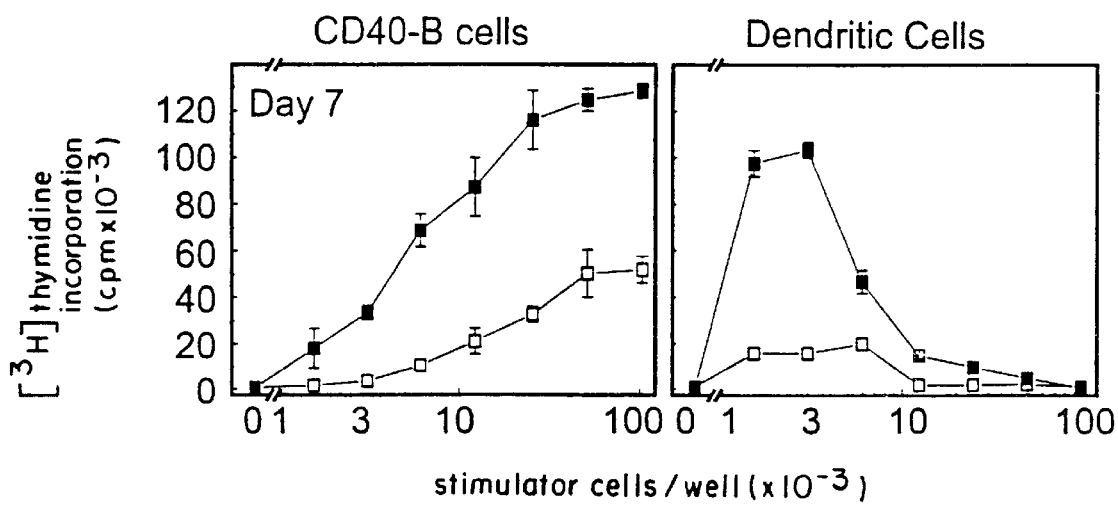

FIGS. 3A–3C show response of allogeneic CD3+ CD4+ CD45RA+ T cells to purified CD40-B cells or DC at Day 3f (FIG. 3A), Day 5 (FIG. 3B) or Day 7 (FIG. 3C). Purified T cells were co-cultured with CD40-activated (CD40-B) B cells or DC generated from peripheral blood. [3H] Thymidine incorporation was assessed for the last 16 hr of a 3-, 5- or 7-day culture. Appropriate controls (CD3+ CD4 CD45RA+ T cells, stimulator cells) were always <2000 cpm. The ability of purified T cells (from other normal donors with unrelated MHC) to proliferate in response to CD40-B cells or DC was tested in a total of 3 experiments.

Figure 4A:
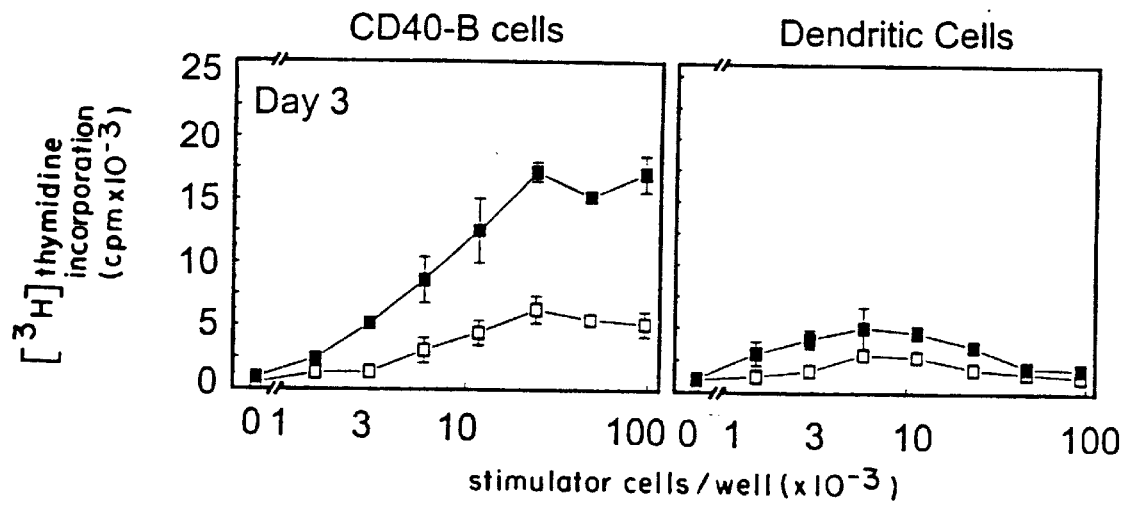
Figure 4B:
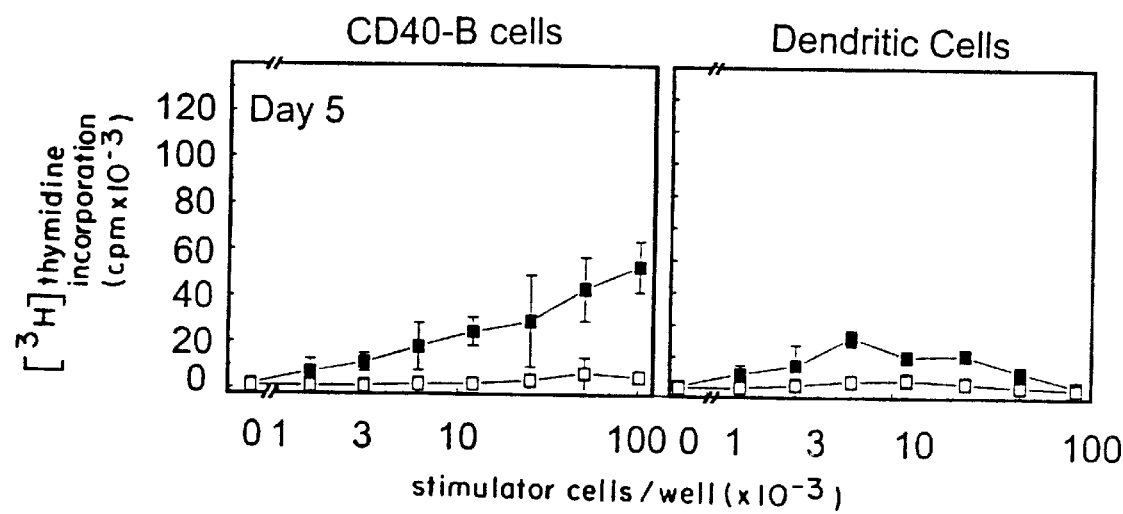
Figure 4C:
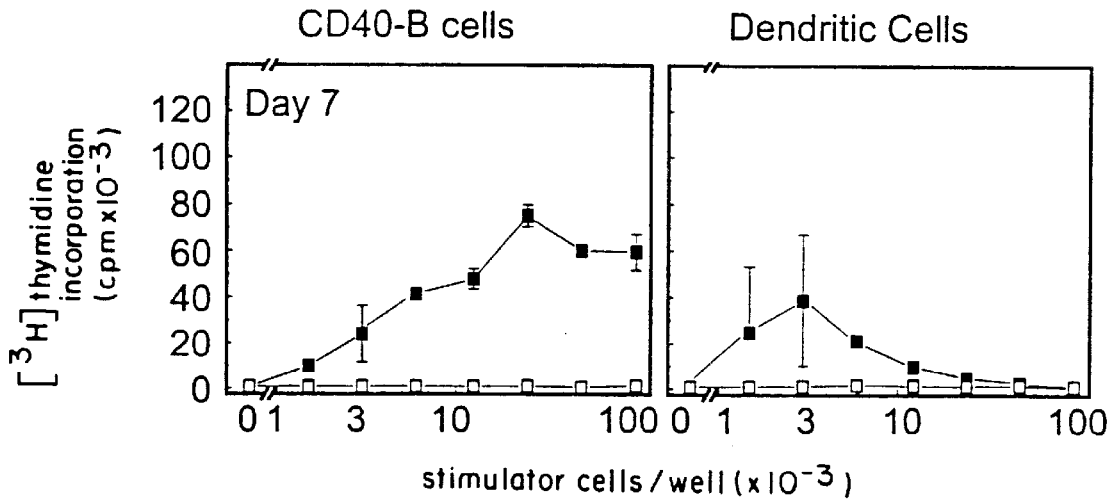

FIGS. 4A–4C show response of allogeneic CD3+ CD8+ T cells to purified CD40-B cells or DC at Day 3 (FIG. 4A), Day 5 (FIG. 4B) or Day 7 (FIG. 4C). Purified T cells were co-cultured with CD40-activated (CD40-B) B cells or DC generated from peripheral blood. [$^3$H]Thymidine incorporation was assessed for the last 16 hr of a 3-, 5- or 7-day culture. Appropriate controls (CD3+ CD8+ T cells, stimulator cells) were always <2000 cpm. The ability of purified CD8+ T cells (from other normal donors with unrelated MHC) to proliferate in response to CD40-B cells or DC was tested in a total of 2 experiments.

Figure 5C:
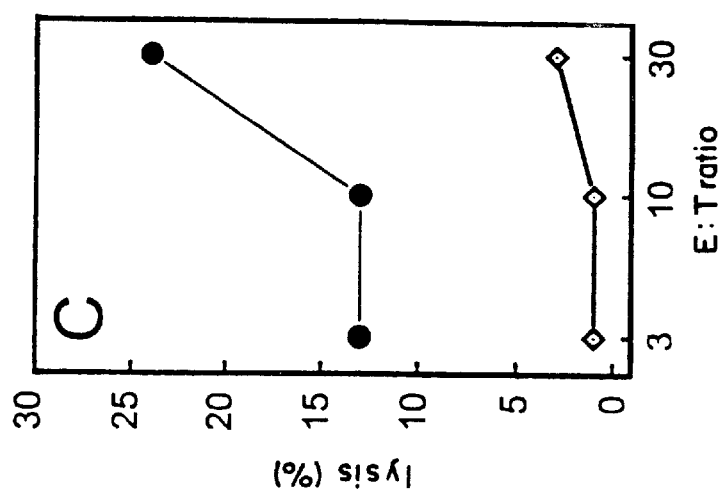
Figure 5B:
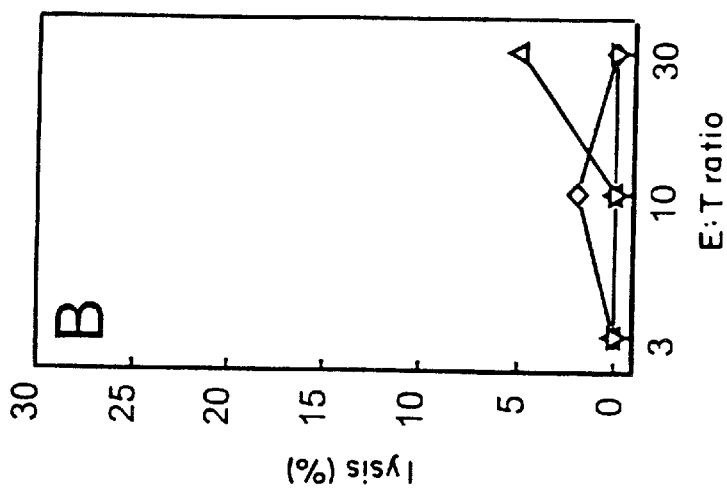
Figure 5A:
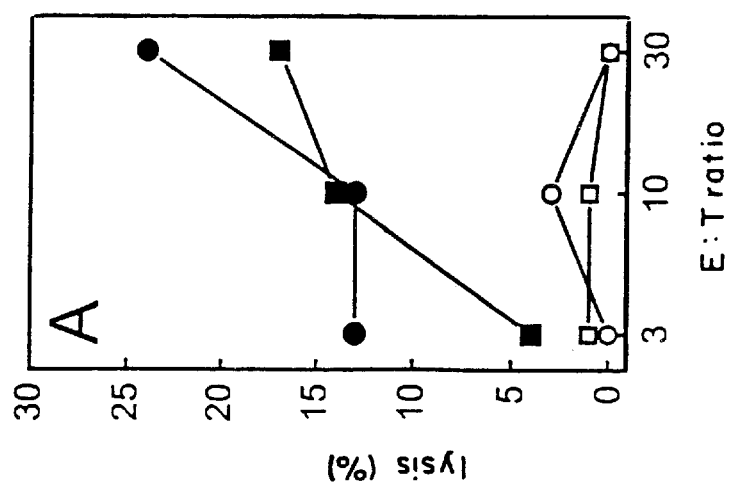

FIGS. 5A–5C show induction of cytotoxic T cells after stimulation with protein-pulsed CD40-B cells. FIG. 5A shows HLA-A*201+ CD40-B cells pulsed with peptide (solid circles and squares), HLA-A*201+ CD40-B cells not pulsed with peptide. FIG. 5B show HLA-A2- CD40-B cells. FIG. 5C show unlabelled peptide pulsed HLA-A*201.cells.

Figure 6:
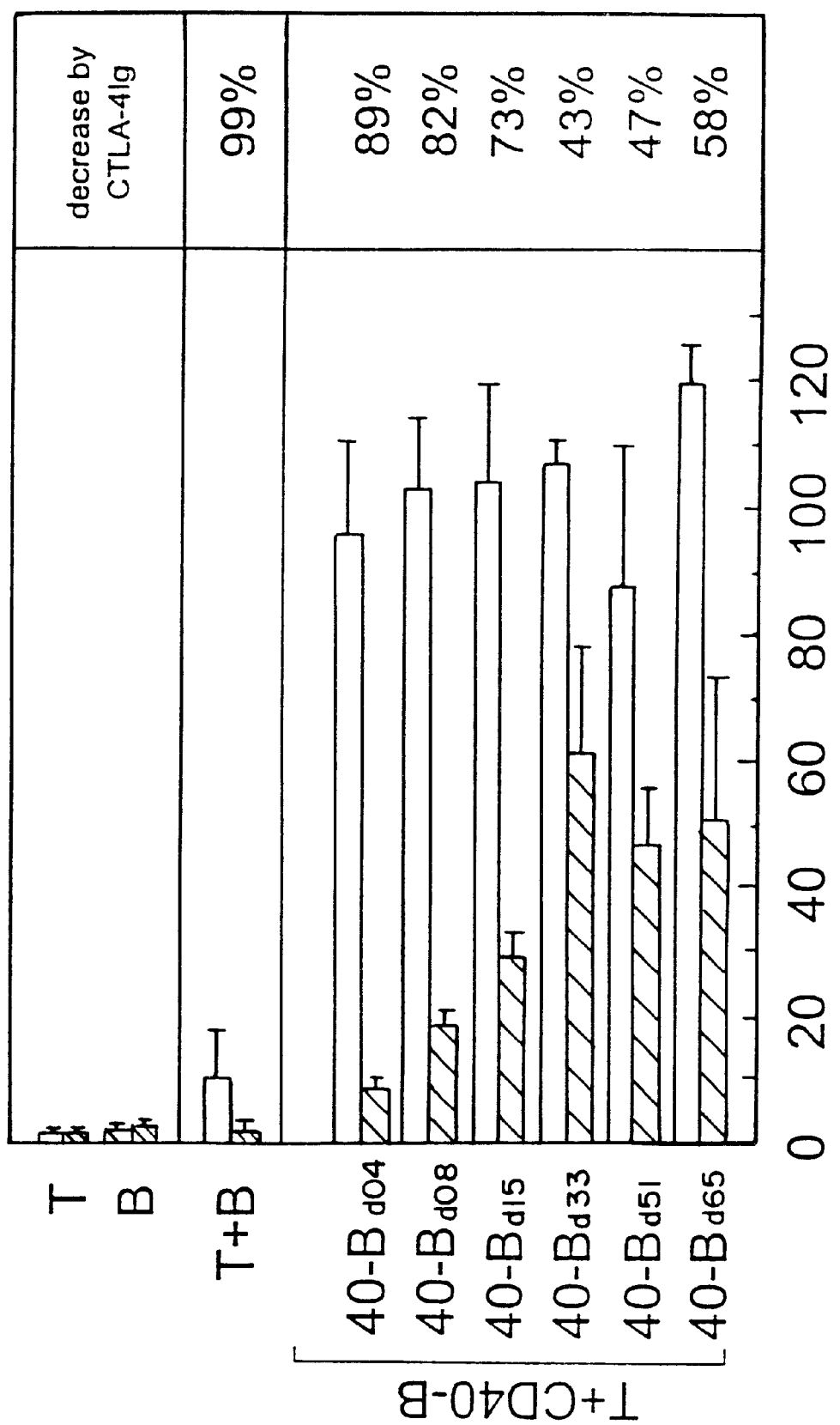

FIG. 6 shows induction of allogeneic T cell proliferation by long-term cultured CD40-B cells. Purified CD3+ CD4+ T cells were co-cultured with CD40-activated (CD40-B) peripheral blood B cells in a final volume of 0.2 ml. Mixed lymphocyte reactions were cultured for 7 days with (grey bars) or without (black bars) the addition of CTLA4-Ig. [$^3$H]Thymidine incorporation was assessed for the last 16 hr of each culture. Appropriate controls (CD3+ CD4+ T cells, stimulator cells) were always <2000 cpm. The ability of purified T cells (from other normal donors with unrelated MHC) to proliferate in response to CD40-B cells was tested in a total of 3 experiments.

FIGS. 7A–7C show phenotypic analysis for surface molecules involved in antigen presentation on CD40-B cells during long-term culture in the CD40L system at day 0 (FIG. 7A), day 15 (FIG. 7B) and day 65 (FIG. 7C). (MIF=mean intensity fluorescence).

Figures 8A, 8B:
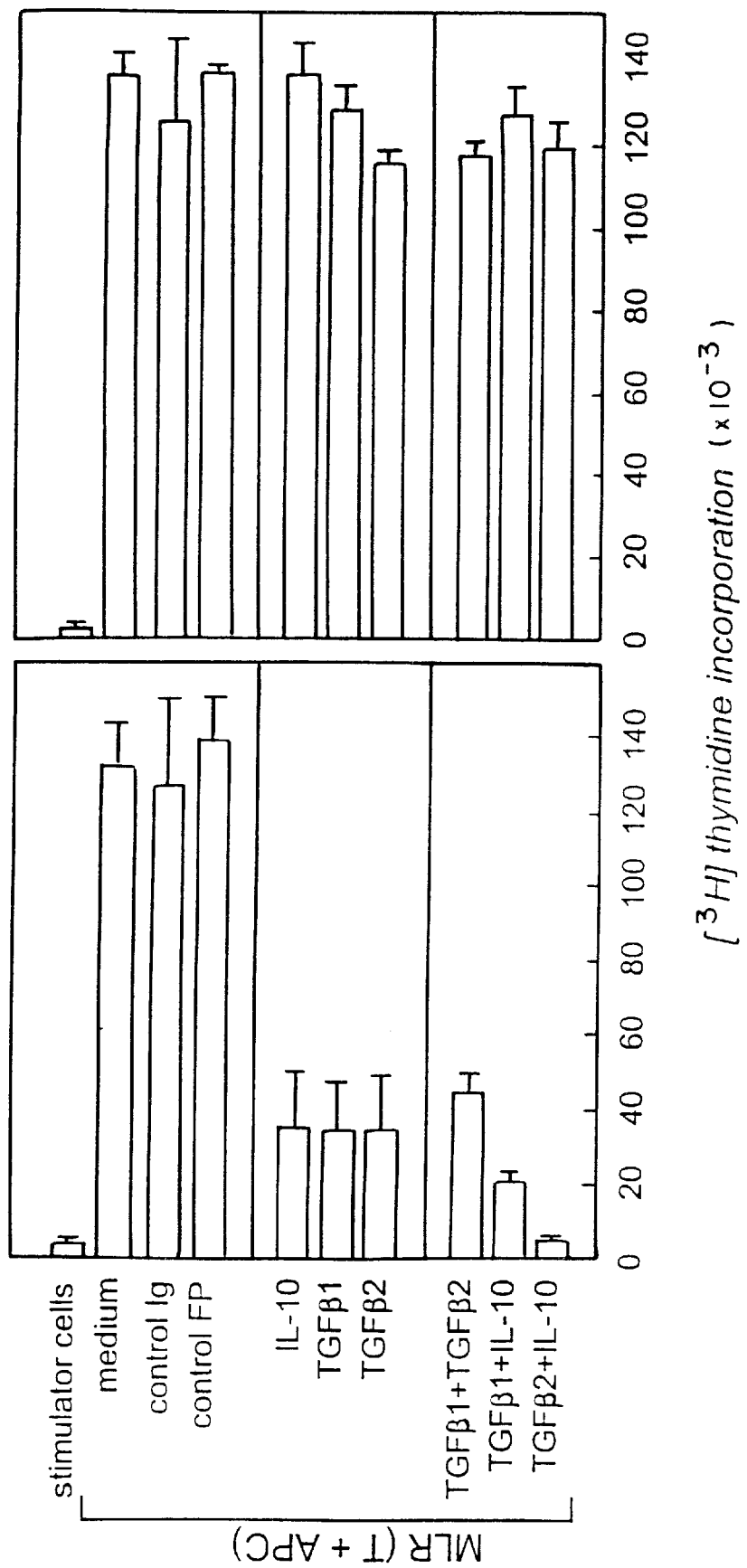

FIGS. 8A–8B show CD40-B cells (FIG. 8A) but not DCs (FIG. 8B) induce an allogeneic T cell proliferation in the presence of immunosuppressive cytokines. Purified CD3+ CD4+ T cells were co-cultured with CD40-activated (CD40-B) peripheral blood B cells or DCs in a final volume of 0.2 ml. IL-10, TGFβ1, TGFβ2 were added at the beginning of co-culture. [$^3$H]Thymidine incorporation was assessed for the last 16 hr of a 6 day culture. Appropriate controls (CD3+ CD4+ T cells, stimulator cells) were always <2000 cpm. The ability of purified T cells (from other normal donors with unrelated MHC) to proliferate in response to CD40-B cells or DC cells was tested in a total of 5 experiments.

DETAILED DESCRIPTION OF INVENTION

We have now discovered that activated B cells can be used as APCs to activate T cells, in a multi-administration protocol. B cells express MHC class I and II and can therefore be used with a wide range of antigens.

While B cells are easily accessible from peripheral blood they have not previously met the criteria for use in the method proposed. Under physiological conditions resting B cells do not express all necessary molecules, such as the costimulatory molecules, to induce a sufficient T cell response. Instead, they were shown to anergize T cells. Only activated B cells express sufficient levels of costimulatory and adhesion molecules to induce T cell proliferation optimally. The major B cell activation pathway is crosslinking of CD40 by CD40L (sometimes also referred to as gp39) that is expressed on activated T cells. However, the methods used to activate B cells also activated T cells. B cells constitute a very small percentage of blood and are difficult, if not impossible, to purify so that no T cells are present. Since, the co-cultured T cells outgrow the B cells, the T cells rapidly become the predominant species being cultured. That problem has been overcome by the following method.

The B cells used can be obtained from a wide range of sources including blood, bone marrow and lymph nodes. For example B cells comprise about 10–15% of blood, 20–25% of lymph nodes, and 40–45% of the spleen.

Preferably, one obtains the B cells from peripheral blood, using about 5 ml to about 500 ml of blood taken from a patient. Preferably, about 50 ml to about 200 ml of blood is taken. More preferably about 50 ml.

For example, one can obtain the B cells from peripheral blood, preferably about 50 ml of blood is taken. One can initially purify the B cells by standard means. For example, peripheral blood mononuclear cells may be isolated by centrifugation through Lymphocyte Separation Medium (Litton Bionetics, Kensington, Md.). Human B Lymphocytes (B cells) may be enriched from PBMC by passage of cells over nylon columns (Wako Chemicals USA, Inc., Richmond Va.) and harvesting of adherent cells. The cells may then be treated with leu-leu methyl ester (Sigma, St. Louis, Mo.) to deplete monocytes and NK cells. The resulting cell population may be analyzed by flow cytometry on an EPICS C (Coulter Electronics, Hialeah, Fla.) to determine the percentage of B cells.

Tonsillar B cells may be prepared from intact tonsils by mincing to produce a tonsillar cell suspension. The cells may then be centrifuged through Lymphocytes Separation Medium, washed twice, and then fractioned on a discontinuous Percoll gradient. Cells with a density greater than 50 percent may be collected, washed twice, and used in proliferation assays.

Measurement of proliferation may be performed by culturing B cells by standard means. For example, culturing B cells in quadruplicate samples in flat-bottomed 96-well microtiter plates at 5×10$^4$ cells per well in complete RPMI medium containing 10 percent fetal calf serum. Supernatants of COS cells expressing (CD40L or control construct, diluted 1:4, plus PMA (10 ng/ml, LC Services, Woburn, Mass.) or 1F5 (anti-CD20, 1 μl/ml) may be added to the cultures, and then B-cell proliferation may be measured by uptake of [$^3$H]-thymidine (6.7 Ci/mmol; DuPont-New England Nuclear, Boston, Mass.) after 5 days of culture and an overnight pulse.

The percent of B cells can be expanded in vivo, if desired, by administration of appropriate cytokines and recruitment growth factors, e.g., IL-4, GM-CSF and IL-3, to the patient prior to removing the B cells.

Methods for obtaining and using B cells are disclosed in European Patent Application 0 585 943A2, and WO 93/08207, the disclosures of which are incorporated by reference.

Once the B cells are obtained by a particular separation technique, they are then cultured under appropriate conditions known in the art. For example, transferrin and insulin help keep B cells alive. Thereafter, the B cells are activated. This involves administration of CD40L. This can be accomplished by use of the soluble form, e.g., sCD40L, or any derivative form such as gp39. Oligomeric forms are preferred over the monomer. See EP 0585943A2 and WO 94/04570. The ligands can be produced by known means or obtained from Immunex Corp. (Seattle, Wash.) or Bristol-Myers Squibb Co. (N.Y., N.Y.). One would also add any cytokine which enhances B cell growth. These are well known and include IL-2, IL-4, IL13, etc. The use of IL-4 is preferred. Growth factors and co-stimulatory molecules are optional. Optionally one can also use monoclonal antibodies that cross-link B cell receptors.

The use of these conditions results in the proliferation and activation of B cells. It also results in the proliferation of any T cells which are present in the culture. Since T cells overgrow B cells, even a small percentage of T cells rapidly predominates. It is virtually impossible to remove all T cells. Further, in order to obtain a sufficient number of B cells at least about 8–10 days of culturing is necessary, preferably about 8–14 days. The B cells can be cultured for extended periods of time by this means. Prior to our invention, it was not practical to culture B cells for such periods because of this problem of T cell overgrowth.

We have found, however, that many immunosuppressive agents, although effecting both T cells and B cells have a sufficient differential window, that T cell proliferation can be selectively depressed, while B cells proliferate.

High purities can be reached by the present method, preferably, without enrichment of B cells prior to culture. Thus, B cells can be cultured, activated and raised in high purity. Preferably, at least 85% pure, more preferably at least 90% pure, still more preferably, at least 95% pure, even more preferably at least 98% pure, and most preferably 99% pure.

Immunosuppressive agents are well known in the art. For example, see Physicians' Desk Reference 50th Edition (1996). They include cyclosporin A (sometimes called cyclosporine) available as Neoral® and Sandimmune®, tacrolimus (previously called FK506) available as Prograf™, azathioprine available as Imuran®, and mycophenolate mofetil available as Cellcept®. Cyclosporin A is preferred.

Cyclosporin A is added to the mixture in a range of $1\times10^{-7}$–$1\times10^{-6}$M, preferably $2\times10^{-7}$–$8\times10^{-7}$, more preferably $5\times10^{-7}$. Ranges can readily be calculated empirically based upon the present disclosure by using titration curves.

The cultures can be grown over extended periods of time —with increasing activated B cell number. Preferably, at least 2 months, more preferably at least 3 months, still more preferably at least 6 months.

Additionally, the activated B cells can be cryopreserved. Cryopreserved material can be used even 5 years later.

The cultured activated B cells or thawed cryopreserved B cells can now be used as APCs. Thereafter, one selects the antigen one wants to present, i.e., the desired antigen. By appropriate selection one can modulate the immune system. For example, one can use an antigen known to T cells, i.e., to which T cells are tolerized to down regulate the T cell specific immune response. Such an approach is beneficial with respect to preventing transplant rejection and treatment of autoimmune diseases. Alternatively, by appropriate selection one can up regulate a desired immune response in one or two—MHC class I and II. Moreover, one can use a cocktail approach, where more than one type of APC is created by contacting different APCs with different antigens.

Preferred target antigens include bacterial antigens, tumor specific antigens, tumor associated antigens, helminthic antigens, antigens from intracellular parasites, viral antigens, antigens of other infectious agents or those induced by other infectious agents (e.g., prion, etc). More preferably the antigen is a viral antigen, tumor specific antigen or tumor associated antigen.

The antigens can be introduced into the APC by a variety of means known in the art. For example, directly by culturing a solution containing one ore more antigens, i.e, pulsing. The antigens may be in the form of MHC I or II peptides—or a proform such as the whole protein, which is allowed to be processed by the cell.

Alternatively, the APC may be provided with a means for synthesizing large quantities of the desired antigen-peptide intracellularly. This can be accomplished by transforming the APC with a nucleic acid segment having a gene encoding the desired peptide operably linked to a promoter. The gene can also be fused to a trafficking signal to direct to the appropriate cellular compartment for presenting and binding to the desired MHC class molecule. See WO 94/04171 which is incorporated herein by reference. Cells can be transformed by a variety of means including viral vectors, nucleic acid delivery vehicles, "naked" DNA, "gene gun", electroporation, $CaPO_4$ precipitation, etc.

Thereafter, the APC which has been prepared can be administered to a selected patient.

The activated B cells can thus be used as APCs from a single culture over an extended period of time. One can combine the APC with a desired antigen or a cocktail of antigens by a variety of techniques well known in the art. For example, one can present the whole antigen, which is then processed, a specific peptide, nucleic acid encoding the antigen or the peptide. One preferred method is to target a nucleic acid encoding a desired antigen to a particular cellular compartment. Another embodiment involves culturing the APC with the protein or peptide (pulsing) for a sufficient time for the APC to process and present the MHC-bound peptide. Thereafter one administers the active APC to the subject. The magnitude of T cell proliferation was dependent on cell number of APCs administered. Because of the large cell number we can obtain over time the T-cell reaction can be greater than that induced by DCs. In addition, we have shown that our CD40-B cells can be pulsed with tumor peptide to induce autologous $CD8^+$ T cells to proliferate and finally kill target cells expressing the antigen. Additionally, the T cell proliferation induced by DCs in the presence of immunosuppressive cytokines is significantly diminished. In contrast, when our CD40-B cells were used under such conditions there was not a reduction in activity.

As a result of our method of culturing B cells, we have created a class of activated B cells, for example, CD40L human B cells (CD40-B), that can be used in a wide range of approaches to present a desired antigen, such as a tumor-associated antigen, to T cells. The resultant CD40-B cells are highly efficient APCs and stimulate allogeneic $CD3^+$ $CD4^+$ $CD45RA^+$ T cells, $CD4^+$ $CD45RO^+$ T cells and $CD3^+$ $CD8^+$ T cells with a higher peak T cell proliferation than DCs from the same donor.

In one embodiment, the patient has a tumor and the desired antigen is a tumor specific or tumor associated antigen. These include melanoma associated antigen, CEA, PSA, breast cancer associated antigen, etc.

The altered APCs are administered to the patient by any suitable means, including, for example, intravenous infusion, bolus injection, and site directed delivery via a catheter. Preferably, the cells obtained from the patient are readministered within a few months of being obtained. However, the APCs can be cryopreserved and used many years later. Generally, from about $10^6$ to about $10^{18}$, more preferably about $10^8$ to about $10^{10}$ APC, most preferably about $10^8$ cells/administration are administered to the patient.

Depending on the use of the APC, various other factors can be delivered, either separately or by transforming the APC. The genetic material that is delivered to the APC progenitors may be genes, for example, those that encode a variety of cytokines, costimulatory factors, other proteins including anticancer agents. Such genes include those encoding various hormones, B7, growth factors, enzymes, cytokines, receptors, MHC molecules and the like. The term "genes" includes nucleic acid sequences both exogenous and endogenous to cells into which a virus vector, for example, a pox virus such as swine pox containing the human B7-1 or B7-2 gene may be introduced. Additionally, it is of interest to use genes encoding polypeptides for secretion from the APCs so as to provide for a systemic effect by the protein encoded by the gene. Specific genes of interest include those encoding interleukin-1, interleukin-2, interleukin-3, interleukin-4, interleukin-5, interleukin-6, interleukin-7, interleukin-8, interleukin-9, interleukin-10, interleukin-11, interleukin-12 etc., GM-CSF, G-CSF, M-CSF, human growth factor, co-stimulatory factor B7, insulin, IL-ira, EPO, the CC (e.g., RANTES) and CXC (e.g., IL-8) chemokines and the like [Baggiolini, et al., *Adv. Immunol.* 55:97–179 (1994); Schall and Bacon, *Curr. Opin. Immunol.* 6:865–873 (1994)], as well as biologically active muteins of these proteins. The gene may further encode a product that regulates expression of another gene product or blocks one or more steps in a biological pathway. In addition, the gene may encode a toxin fused to a polypeptide, e.g., a receptor ligand, or an antibody that directs the toxin to a target, such as a tumor cell.

One can also deliver these proteins by direct administration.

These compounds can be administered directly, e.g., intra-arterially, intramuscularly, or intravenously, or nucleic acid encoding the protein may be used.

The nucleic acid encoding a cytokine, for example, can be administered to the tumor or a blood vessel feeding the tumor via a catheter, for example, a hydrogel catheter. The nucleic acid also can be delivered by injection directly into the target tissue using known methods.

The term "effective amount" means a sufficient amount of APC, additional compound, e.g. nucleic acid delivered to produce an adequate level, i.e., levels capable of inducing the desired immune reaction.

For example, with the APC the important aspect is the level of antigen presented. Additionally, the "boost" amounts of APC can vary depending upon the treatment regiment and the individual patient's reaction. Typically, lower levels of APCs can be used for later administration then the initial 2 or 3 administrations. The APC is administered to the patient, preferably a human at fixed intervals. These typically range from 7 days to 2 months, more preferably 7 to 14 days. One adminsters the APC at additional intervals of 2–8 adminstrations, preferably 4–6 administration.

Our CD40-B cells when pulsed with a desired antigen such as a tumor peptide elicit a peptide specific T cell response of autologous cytotoxic $CD8^+$ T cells. These activated B cells do not lose their APC capacity during long-term culture and/or cryopreservation, can be obtained from small amounts of peripheral blood in a single procedure, and expanded to sufficient quantities for multiple administration over extended periods. The CD40-Bs produced herein are clearly superior to DCs under immunosuppressive culture conditions, since cytokines that are immunosuppressive such as IL-10 and/or TGFβ, did not reduce T cell proliferation in the presence of allogenic T cells and CD40-B cells. In contrast, when DCs were used with the allogenic T cells, cytokines for example, the combination of the IL-10 and TGFβ completely blocked T cell proliferation. Therefore, by using the present method large numbers of activated B cells can be obtained, they can be used as APCs and they can be used under a wide range of conditions—many of which are not useful with other APCs such as DCs.

The existence of a range of antigen, e.g., tumor-specific or tumor-associated antigens and the presentation of such a desired peptide derived from these antigens by MHC class I and II molecules has led to a revival in interest in T cell mediated tumor immunity over the last few years [Lanzavecchia, 1993 #84; Pardoll, 1992 #85; Pardoll, 1993 #86; Pardoll, 1993 #87; Pardoll, 1994 #88; Boon, 1994 #89; Boon, 1994 #90]. For example, $CD8^+$ T cells can kill tumor cells after recognition of MHC/peptide complexes on the surface of the tumor cells. In addition, there is not only an important role for $CD8^+$ T cells, but also for $CD4^+$ T cells as recently reviewed by S. Topalian [Topalian, 1994 #91]. However, since many cells, for example tumor cells, are rather poor antigen presenting cells, often expressing low levels or lacking MHC class I molecules and generally lacking MHC class II and costimulatory molecules, the initiation of a desired immune response, particularly an antitumor response, requires separate administration of APCs, typically over an extended course of administrations. One selects the desired antigen to use with the APC, such as a viral antigen, a parasitic antigen, a tumor-specific antigen or TAA for appropriate presentation of the tumor-specific or associated peptides by APCs. Because of their tissue distribution and their ability to migrate from tissues, such as the skin, to lymphoid organs DCs are believed to be the one major APCs particularly in taking up, processing and presenting tumor-antigen derived peptides. Moreover, DCs have been shown to express high levels of MHC molecules as well as costimulatory molecules. They have been demonstrated as efficient APCs in vitro and in vivo. Therefore, over the past years great effort was undertaken to isolate, purify and amplify DCs in vitro. Although such efforts have been successful, expansion of sufficient numbers of DCs requires culture in multiple cytokine containing cocktails for considerable periods of time. Multiple different strategies have been described to obtain larger quantities of DCs for generating an immune reaction such as in vaccination strategies. For example starting from 1 ml of a bone marrow (BM) aspirate $1.7 \times 10^6$ mature DCs can be obtained after 14 days of culture in a 3 cytokine cocktail. In another method $1.7 \times 10^7$ DCs can be obtained from $1 \times 10^6$ PBSC but a period of more than 30 days was necessary. However, DCs effectiveness peaks at 21 days and begins to go down.

In contrast we have shown that by our methodology a 350-fold expansion (range 225–550x) of $2.5 \times 10^6$ B cells from 50 ml of peripheral blood ($0.75 \times 10^9$ CD40-B cells, range $0.5$–$1.13 \times 10^9$ cells) over 14 days can be obtained. Because the B cells are not as effective on a cell to cell basis, an estimated 5 fold administration of CD40-B cells is necessary to induce equivalent T cell proliferation. Thus, one would need either $2\times10^7$ PBSC or 200 ml of BM to get an equivalent dose to DCs. We have found that at 14 days of culturing we get about the amount necessary. However, thereafter, the CD40-B cell numbers then began to go consistently higher than that for DCs and continue to go up after 21 days. While both methods are invasive, in a multiple administration protocol, our approach is considerably less invasive. Thus, it is preferred where there is a multi-administration protocol, e.g., 3–10 shots, each shot at a fixed interval of 7 days to 2 months.

Although the role of B cells in priming T cell responses is still controversial, in B cell knockout mice, priming of $CD4^+$ T cells with soluble antigen fails for either clonal expansion or delivery of immunological help for antibody production, indicating that B cells play an important role in the induction of productive immunity. In addition, a recent report demonstrated that recombinant vaccinia-infected B cells activated with CD40 mAb could activate a $CD8^+$ T cell mediated CTL response against a known immunogenic vaccinia peptide epitope in vitro [Khanna, 1993 #92]. However, the role of B cells in the induction of $CD8^+$ T cells in vivo is not yet fully defined. However, we have shown our CD40-B cells do act as APCs and cause immune reactions.

Whereas T cell proliferation induced by DCs is significantly decreased in the presence of immunosuppressive cytokines such as TGFβ or IL-10. Indeed, a TGFβ and IL-10 combination can virtually abolish T cell proliferation. That is not the case with the present method. By contrast, CD40-B cell induced T cell proliferation is not significantly altered by the addition of these cytokines. It was reported that IL-10 can also downregulate the expression of MHC class II monocytes but not on EBV transformed human B cell lines [EBV-LCL] and that such downregulation strongly reduced T cell proliferation when stimulated with these monocytes [de Waal Malefyt, 1991 #27].

Not only EBV-LCL are unaffected by either IL-10 or TGFβ but also our CD40-B cells. Accordingly, the antigen-presenting capacity might be regulated differentially in different population of APCs by the expression of cytokines in the respective microenvironment. In the skin e.g. a major source of IL-10 are keratinocytes [Enk, 1992 #83; Beissert, 1995 #78; Enk, 1995 #79. Rivas, 1992 #82]. Although not wishing to be bound by theory we believe that the antigen presenting capacity of skin DCs (Langerhans cells) and blood derived DCs might be tightly regulated by paracrine secreted immunosuppressive cytokines such as IL-10 [Peguet-Navarro, 1994 #80; Ullrich, 1994 #81].

Besides the advantages of CD40-B cells as APCs for generating an immune reaction such as useful for vaccination approaches, we have preliminary data using RT-PCR at a detection level of 1 in $10^5$ cells indicating that no tCD40L cells are present in our B cell preparation after a specific procedure to delete the transfectants. There is only one likely exclusion to make for the vaccination approach with activated B cells. In case of B cell malignancies, the tumor cells themselves would be expanded in the system and therefore this approach is not preferable.

As discussed above, where the APC is transformed, the nucleic acids are introduced into the APC by any method which will result in the uptake and expression of the nucleic acid by the cells. These can include vectors, liposomes, naked DNA, adjuvant-assisted DNA, catheters, gene gun, etc. Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller, A. I. et al., *J. Neurochem*, 64: 487 (1995); Lim, F., et al., in DNA Cloning: *Mammalian Systems*, D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci USA*: 87:1149 (1990)], Adenovirus Vectors [LeGal LaSalle et al., *Science*, 259:988 (1993); Davidson, et al., *Nat. Genet* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofecton, cell microinjection, viral vectors and use of the "gene gun".

To simplify the manipulation and handling of the nucleic acid encoding the protein, the nucleic acid is preferably inserted into a cassette where it is operably linked to a promoter. The promoter must be capable of driving expression of the protein in cells of the desired target tissue. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., *Molecular Cloning: A Laboratory Manual,* Cold Spring Harbor Laboratory press, (1989). The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

If desired, the preselected compound, e.g. a nucleic acid such as DNA may also be used with a microdelivery vehicle such as cationic liposomes and adenoviral vectors. For a review of the procedures for liposome preparation, targeting and delivery of contents, see Mannino and Gould-Fogerite, *Bio Techniques,* 6:682 (1988). See also, Feigner and Holm, *Bethesda Res. Lab. Focus,* 11 (2):21 (1989) and Maurer, R. A., *Bethesda Res. Lab. Focus,* 11 (2):25 (1989).

Replication-defective recombinant adenoviral vectors, can be produced in accordance with known techniques. See, Quantin, et al., *Proc. Natl. Acad. Sci. USA,* 89:2581–2584 (1992); Stratford-Perricadet, et al., *J. Clin. Invest.,* 90:626–630 (1992); and Rosenfeld, et al., *Cell,* 68:143–155 (1992).

The effective dose of the nucleic acid will be a function of the particular expressed peptide, the target tissue, the patient and his or her clinical condition. Effective amount of DNA are between about 1 and 4000 µg, more preferably about 1000 and 2000, most preferably between about 2000 and 4000.

The present invention also includes pharmaceutical products for all the uses contemplated in the methods described herein. For example, there is a pharmaceutical product, comprising the APCs in a physiologically acceptable administrable form.

The present invention further includes a kit for the in vivo systemic introduction of an APC and a desired antigen-either as the antigen-peptide or nucleic acid encoding the same into a patient. In the kit the APC is preferably cryopreserved. Such a kit includes a carrier solution, nucleic acid or mitogen, and a means of delivery, e.g., a catheter or syringe. The kit may also include instructions for the administration of the preparation.

All documents mentioned herein are incorporated by reference herein in their entirety.

The present invention is further illustrated by the following examples. These examples are provided to aid in the understanding of the invention and are not construed as a limitation thereof.

EXAMPLES

Material and Methods
Human Peripheral Blood Lymphocytes

Human peripheral blood lymphocytes from healthy volunteers were obtained after venipuncture (PBL) or after leukophoresis (LP). All specimens were obtained following approval by Institution Review Committees and informed consent for blood donations was obtained from all volunteers.

Purification of T Cells

Mononuclear cells (PBMC) from PBL or LP were isolated by Ficoll-Isopaque density centrifugation. Purification of T cell populations was performed as previously described [Schultze, 1995 #28], and purity assessed by immunophenotyping. To obtain $CD3^+$ $CD4^+$ $CD45RA^+$ T cells PBMC were twice magnetic bead depleted using antibodies against CD20 (clone B1), CD19 (clone B4), CD14 (clone Mo2), CD11a (clone M1), CD56 (clone 3B8), and CD45RO (clone UCHL1). To obtain $CD3^+$ $CD4^+$ $CD45RO^+$ T cells PBMC were twice magnetic bead depleted using antibodies against CD20, CD19, CD14, CD11, CD56, and CD45RA. By depleting cells positive for CD20, CD19, CD14, CD11, CD56 and CD4 $CD3^+$ $CD8^+$ T cells were obtained. Purity of $CD3^+$ $CD4^{30}$ $CD45RA^+$ T cells >97%, $CD3^+$ $CD4^+$ $CD45RO^+$ T cells (>99%) or $CD3^+$ $CD8^+$ T cells was assessed by immunophenotypic analysis.

Immunofluorescence Studies

Surface expression of molecules was detected by FACS analysis using the following mAbs conjugated with FITC or PE; CD3-FITC, CD4-PE, CD8-PE, CD19-PB, CD20-PE, CD56-PE, CD83-PE (HB15), anti-MHC class II-PE (Coulter, Miami, Fla.), CD54-PE (Becton Dickinson, Mountain view, Calif.), CD58 FITC (Southern Biotechnology, Birmingham, Ala.) CD14-FITC, CD33-PE (Dako, Carpinteria, Calif.). For detection of B7-1 clone YB2.C4 (Repligen Corporation, Cambridge Mass.) were used and for B7-2 (B70-PE, clone IT2.2) (Pharmingen. Calif.). CTLA4-Ig FITC and control-Ig fusion protein (FP-Ig) were provided by Repligen. Hybridomas for anti-MHC class I and CD40 were obtained from ATCC. Analysis was performed on a Coulter Epics XLS and saved as list mode files. 1000 events were analyzed for every parameter.

Cytokines

Human rhIL-4 was a generous gift of Dr. Widmer (Immunex, Seattle, Wash.). Human GM-CSF, IL-10, TGFβ1 and TGFβ2 were purchased from Genzyme (Cambridge, Mass.). IL-2 was a kind gift of Dr. M. Robertson (DFCI, Boston, Mass.).

Peptides

The tyrosinase peptide YMNGTMSQV (SEQ ID NO: 1)(369–377) and the Influenza A matrix peptide GILG-FVFTL (SEQ ID NO: 2)(58–66) were synthesized on a multiple peptide synthesizer (Abimed AMS 422) and HPLC purified by the Dana-Farber molecular core facility. Peptides were stored in DMSO at 100 mg/ml at −70° C. From this stock solution, peptide was dissolved in PBS at 1 mg/ml and adjusted to pH 7 before use in cytotoxicity experiments or CTL induction experiments [Visseren, 1995 #75].

Induction and Expansion of Activated B Cells (CD40-B Cells)

PBMC were cultured at $2\times10^6$ cells/ml on NIH3T3 cells transfected with the human CD40 ligand (t-CD40L) (REF Schultze) in IMDM (Gibco BRL) supplemented with 2% FCS, 0.5% BSA (Sigma), 50 µg/rnl human transferrin (Boehringer Mannheim), 5 µg/ml bovine insulin (Sigma) and 15 µg/ml ENTAMICIN (Gibco BRL) at 370C in 5% $CO_2$. IL-4 was added at a concentration of 2 ng/ml (100 U/ml) and cyclosporin A (CsA) at $0.5\times10^{-6}$ M. Cells were transferred to new plates with fresh irradiated tCD40L cells every third day. For functional analysis cultured cells (CD40-B) were washed 2× in IMDM, kept on ice for 1 hour in IMDM and then finally washed and resuspended in RPMI supplemented with 5% human serum, 2 mM Glutamine, 15 µg/ml Gentamicin (RPMI-5). For expansion CD40-B cells were cultured on 6-well plates at a concentration of $1\times10^6$ cells/ml and recultured every third day on freshly prepared plates with t-CD40L cells. Every second time, when recultured, CD40-B cells were Ficoll-density centrifuged to remove non-viable cells. Every time, when CD40-B cells were recultured, only a small proportion of cells was recultured and remaining cells either used for analysis or cryopreserved. The potential total increase was then calculated. Experiments using $10^8$–$10^9$B cells cultured in tissue culture flasks (162 $cm^2$, Costar) were performed to show, that expansion was similar under large scale conditions (REF manuscript in preparation).

Isolation of Dendritic Cell (DC) Precursor and Culture of DCs

Dendritic cells derived from peripheral blood were obtained following a protocol previously described [Romani, 1994 #71]. Briefly, after Ficoli-density centrifugation, DC precursor were enriched by the following procedure: first macrophages were removed by plastic adherence for 1 hr. Since DC precursor are loosely adherent [Romani, 1994 #71] they were removed with the non-adherent cells by vigorously washing the plates. To further enrich for DC precursor T, B and NK cells were removed by MBD. The remaining cells were then cultured in IMDM (Gibco BRL) supplemented with 5% FCS, 50 µg/ml human transferrin (Boehringer Manntheim), 5 µg/ml bovine insulin (Sigma) and 15 µg/ml Gentamicin (Gibco BRL) at 37° C. in 5% $CO_2$ for 6 days. GM-CSF (500 U/ml) and IL-4 (10 ng/ml, respectively 500 U/ml) were added throughout the whole culture period. For further analysis DC were removed from the culture plates by vigorously washing. Cells were washed twice in PBS and resuspended in either PBS supplemented with 0.5% BSA for phenotypic analysis or RPMI-5 (HS) for functional analysis.

Allogeneic Mixed Lymphocyte Reaction (Allo-MLR)

$CD3^+$ $CD4^+$ $CD45RA^+$ T cells or $CD3^+$ $CD4^+$ $CD45RO^+$ T cells or $CD3^+$ $CD8^+$ from healthy individuals were plated at $1 \times 10^5$ T cells/well with $10^1$ to $10^5$ irradiated (32 Gy) DCs or CD40-B cells/well in 96 well round-bottom plates (Nunc, Roskilde, Denmark) in a final volume of 200 µl. Cultured DCs and CD40-B cells were washed twice at 4° C. in PBS before use. To assess the function of costimulatory molecules during the MLR, DCs or CD40-B cells were preincubated with CTLA4-Ig (10 µg/ml) for 30 min at 4° C. prior addition to the T cells A control-Ig (FP-Ig) were used as appropriate controls. To measure the influence of IL-10, TGFβ1 and TGFβ2 on APC capacity of DCs and CD40-B cells, allogeneic MLRs were performed in the presence of IL-10 (10 ng/ml), TGFβ1 (5 ng/ml), TGFβ2 (5 ng/ml) or their combinations. These concentrations were found to be the minimal concentrations in titration experiments to reduce T cell proliferation induced by CD3 mAb in the presence of CD28 mAbs (data not shown). Cultures in triplicate were incubated in RPMI-5 at 37° C. in 5% $CO_2$ for 3, 5 or 7 days. Cells were pulsed with [$^3$H]Thymidine (1 mcCi, Du Pont, Boston, Mass.) for the last 16 hours of the 3, 5 or 7 day culture period. Cells were then harvested onto filters and the radioactivity measured in a beta plate liquid scintillation counter (Pharmacia, Piscataway, N.J.).

In vitro CTL Response Induction

CTL induction in vitro was performed as described previously [Visseren, 1995 #75]. CD40-B cells of HLA-A*0201$^+$ donors (Table 1) were collected from culture, washed twice in PBS and cultured overnight at 26° C. in RPMI-5. Subsequently CD40-B cells were loaded with peptide (50 µg/ml) in the presence of human β2-microglobulin (3 µg/ml), irradiated and added to purified $CD3^+$ $CD8^+$ T cells (>98%) of the same donor in T cell culture medium containing rh IL-7 (10 ng/ml). At day 7, T cell cultures were harvested, ficoll density centrifuged to remove non-viable cells, washed twice and restimulated with fresh peptide-pulsed CD40-B cells and IL-7. IL-2 was added at days 10–12 (10 IU/ml). For restimulation of T cells, CD40-B cells were pulsed for 2 hrs at 37° C. with peptide (10 µg/ml) and β2-microglobulin (3 µg/ml). Cultures were restimulated on day 14 with fresh peptide pulsed CD40-B and rh IL-7. Again IL-2 was added (days 18–20). To further expand T cells, IL-2 at a higher concentration was added at day 21 (100 IU/ml). After 25–28 days of culture the lytic activity of the bulk cultures was tested.

TABLE 1

Table x:
Cytotoxicity of CD8+ T cells stimulated with autologous tyrosinase peptide pulsed CD40-B cells

| Source of target cells | | E:T | Donor 1 | Donor 2 | Donor 3 | Donor 4 | Donor 5 |
|---|---|---|---|---|---|---|---|
| Donor 1 | CD40-B | 30 | 2 | 1 | 19 | −3 | n.d. |
|  |  | 10 | −3 | 3 | 16 | −1 |  |
|  |  | 3 | −7 | 2 | 8 | 4 |  |
|  | CD40-B + Tyrosinase peptide | 30 | 42 | 41 | 39 | 27 | n.d. |
|  |  | 10 | 38 | 44 | 31 | 27 |  |
|  |  | 3 | 30 | 31 | 21 | 20 |  |
|  | CD40-B + Influenza A peptide | 30 | −4 | −2 | 7 | −5 | n.d. |
|  |  | 10 | −7 | −4 | 0 | −4 |  |
|  |  | 3 | −7 | −11 | 0 | −5 |  |
| Donor 3 | CD40-B | 30 | 1 | 1 | 4 | 5 | n.d. |
|  |  | 10 | −4 | 7 | 14 | 1 |  |
|  |  | 3 | 1 | 4 | 12 | 2 |  |
|  | CD40-B + Tyrosinase peptide | 30 | 30 | 39 | 19 | 14 | n.d. |
|  |  | 10 | 29 | 32 | 18 | 15 |  |
|  |  | 3 | 20 | 28 | 15 | 13 |  |
| Donor 4 | CD40-B | 30 | −5 | −5 | 1 | −6 | n.d. |
|  |  | 10 | −10 | 3 | 1 | −4 |  |
|  |  | 3 | −8 | −4 | 0 | −7 |  |
|  | CD40-B + Tyrosinase peptide | 30 | 36 | 40 | 29 | 21 | 25 |
|  |  | 10 | 36 | 44 | 19 | 20 | 20 |
|  |  | 3 | 21 | 26 | 16 | 17 | 20 |
|  | CD40-B + Influenza A peptide | 30 | 7 | 4 | 10 | 9 | n.d. |
|  |  | 10 | 5 | 0 | 6 | 11 |  |
|  |  | 3 | −6 | −4 | 1 | 3 |  |
|  | PHA blasts | 30 | −8 | 1 | 2 | 8 | 7 |
|  |  | 10 | −8 | 1 | 3 | 2 | 4 |
|  |  | 3 | −6 | 2 | 5 | 5 | 6 |
| Donor 5 | CD40-B | 30 | 17 | 15 | 26 | 4 | 30 |
|  |  | 10 | 17 | 15 | 7 | −3 | 12 |
|  |  | 3 | 4 | −1 | 9 | 2 | 6 |
|  | CD40-B + Tyrosinase | 30 | 51 | 39 | 26 | 22 | 44 |
|  |  | 10 | 38 | 52 | 23 | 13 | 21 |
|  |  | 3 | 19 | −32 | 6 | −1 | 15 |
|  | PHA blasts | 30 | 1 | 8 | −5 | −2 | −2 |
|  |  | 10 | −3 | 7 | 5 | −5 | −2 |
|  |  | 3 | −3 | −1 | 6 | −4 | −2 |

TABLE 1-continued

Table x:
Cytotoxicity of CD8+ T cells stimulated with autologous tyrosinase peptide pulsed CD40-B cells

| Source of target cells | | E:T | Donor 1 | Donor 2 | Donor 3 | Donor 4 | Donor 5 |
|---|---|---|---|---|---|---|---|
| Melanoma I | K013 HLA-A201* | 30 | 67 | 64 | 67 | 64 | 62 |
| | | 10 | 54 | 63 | 67 | 58 | 50 |
| | | 3 | 40 | 59 | 29 | 45 | 28 |
| | K013 HLA-A201* + | 30 | 49 | 44 | 51 | 45 | 43 |
| | Tyrosinase peptide | 10 | 46 | 44 | 47 | 41 | 44 |
| | | 3 | 42 | 33 | 45 | 34 | 40 |
| Melanoma II | K015 HLA-201* | 30 | 59 | 60 | 34 | 54 | 40 |
| | | 10 | 39 | 43 | 42 | 27 | 40 |
| | | 3 | 0 | 16 | 25 | 5 | 17 |
| Allogeneic I | CD40-B HLA-A2- | 30 | −11 | −8 | −13 | −24 | n.d. |
| | | 10 | −6 | 6 | −10 | −7 | |
| | | 3 | −2 | −5 | −10 | −10 | |
| Allogeneic II | CD40-B HLA-A2- | 30 | −13 | −7 | 1 | −11 | n.d. |
| | | 10 | 1 | 1 | −4 | −9 | |
| | | 3 | −7 | −7 | −9 | −2 | |

JAM-test

T cell cytotoxicity to peptide-pulsed APCs was assessed using a modification of a previously published method. [Matzinger, 1991 #40] As target cells, CD40-B cells were harvested from culture, washed twice by centrifugation in PBS and resuspended in RPMI-5. The cells were incubated with [$^3$H]Thymidine with or without peptide (10 μg/ml) and b2-microglobulin (3 μg/ml) overnight at 37° C. Target cells were again washed by centrifugation and mixed with various numbers of effectors in a final volume of 0.2 ml of RPMI-5 in round-bottom microtiter plates. After 4–8 hr of incubation, the plates were harvested and the radioactivity was determined in a b counter. Percent specific cytotoxicity was determined using the following equation.

% specific DNA loss=(S-E)/S×100 whose E=experimentally retained DNA in the presence of T cells (in cpm).

Sectioned DNA in the absence of T cells (spontaneous).

Spontaneous lysis was determined by incubating the targets alone, in the absence of effector T cells. Maximum lysis was determined by incubating the target cells with 0.2% Triton X-100 (Sigma). All determinations were done in triplicates and the standard errors of the means were always <10% of the value of mean.

Results

Figures 1A, 1B:
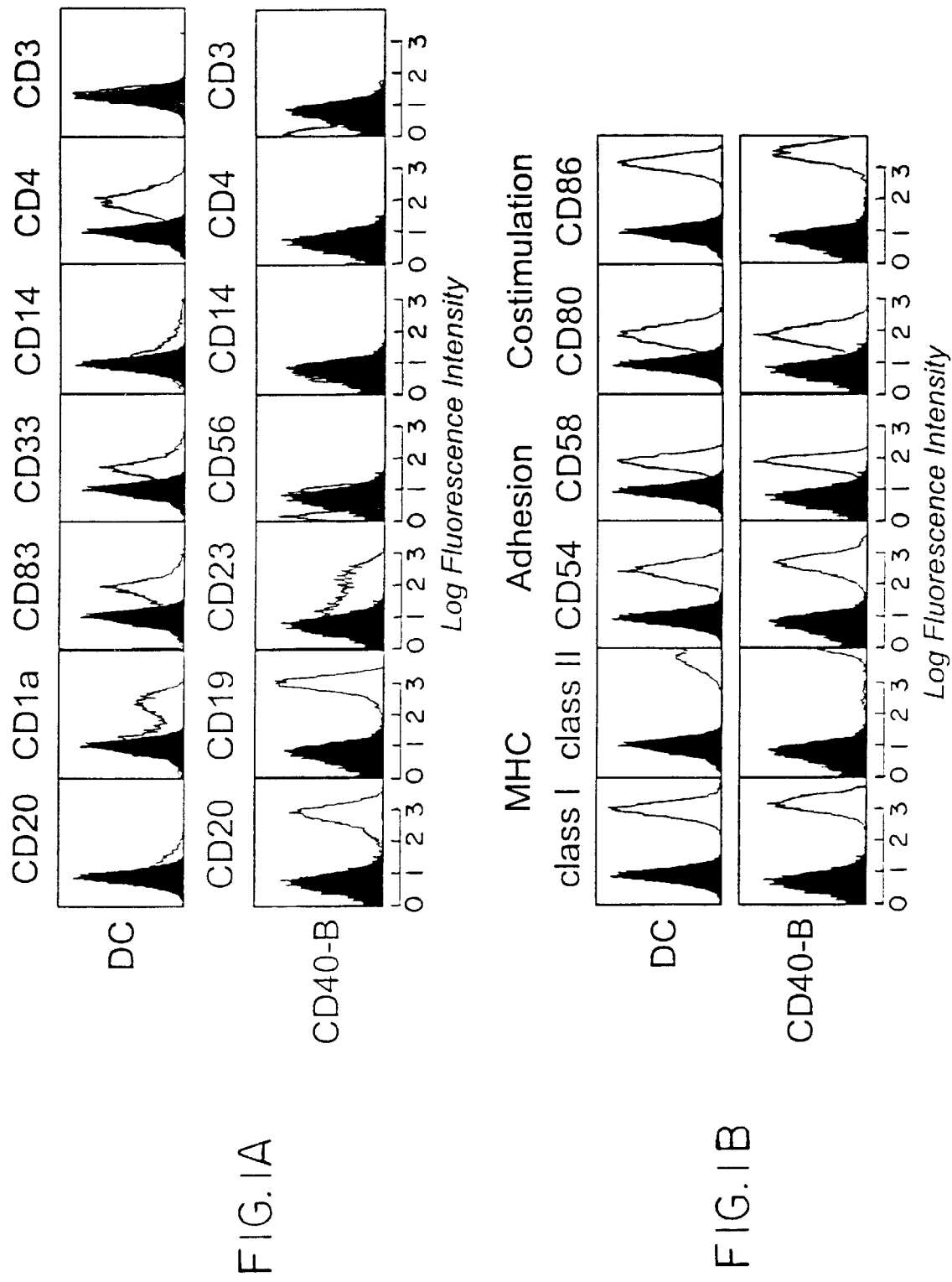
FIGS. 1A and 1B show immunophenotypic analysis of CD40 activated B cells (lower) and DC cells (upper).

Expression of MHC, adhesion and costimulatory molecules on CD40 activated B cells is comparable to in vitro activated peripheral blood dendritic cells. DCs are known to express extremely high levels of molecules necessary for antigen presentation. To determine whether the levels of these surface molecules on B cells after activation is comparable to DCs we purified B cells from peripheral blood and activated them by culture on NIH3T3 cells transfected with the human CD40 ligand (t-CD40L) in the presence of IL-4. At the same time we generated DCs from peripheral blood and cultured them with IL-4 and GM-CSF (REF Schuler) prior to phenotypic and functional analyses. After 5–7 days of culture DC and activated B cells (CD40-B) were harvested, Ficoll density centrifuged to remove dead cells and washed twice subsequently. Phenotypic analysis revealed, that the cells cultured with GM-CSF and IL-4 were more than 80% DCs as determined by FACS analysis of surface molecules. These cells (FIG. 1A) expressed CD83 (HB15) (85%) [Zhou, 1995 #77]), CD1a (49%), CD33 (67%) and CD4 (90%), but lacked other lineage marker such as CD20 for B cells, CD3 for T cells and CD56 for NK cells. A small percentage of macrophages (9%) expressing CD14 could be detected in this cultures. B cells cultured for 5–7 days in the CD40L system expressed high levels of CD20 (95%) and CD19 (94%), and most of the cells expressed CD23 (69%) (FIG. 1A). There were no detectable CD56$^+$, CD14$^+$ or CD3$^+$ cells present. Efficient antigen presenting capacity is phenotypically characterized by high levels of expression of MHC, adhesion and costimulatory molecules. As shown in FIG. 1B, CD40-B cells as well as DCs expressed equivalently high levels of MHC class I and II molecules as well as very high levels of adhesion molecules such as CD54 (ICAM-1) and CD58 (LFA-3). Moreover, the level of expression of the two major costimulatory molecules CD80 (B7-1) and CD86 (B7-2) on CD40-B cells was as high as on DCs.

Not only allogeneic CD4$^+$ CD45RO$^+$ T cells but also CD4$^+$ CD45RA$^+$ T cells and CD8$^+$T cells are very efficiently stimulated by CD40-B cells. From the phenotypic analysis one would predict that CD40-B cells might be as efficient in presenting antigen as DCs. To assess their antigen presenting capacity we used highly purified allogeneic T cells and stimulated them with CD40-B or DC cells from the same donor. CD4$^+$ T cells were further divided into CD45RA$^+$ (>97%) or CD45RO$^+$ (>99%) T cells and individually stimulated. In addition CD8$^+$ T cells (>98%) were also tested for their proliferative response to CD40-B or DCs. Allogeneic T cells ($10^5$ cells/well) were incubated with increasing numbers of irradiated (32 Gy) CD40/B or DCs and T cell proliferation assessed after 3, 5 and 7 days. As shown in FIG. 2, CD40-B cells (left panel) induced a dramatic T cell proliferation of CD4$^+$ CD45RO$^+$ T cells peaking at day 7 and the magnitude of proliferation clearly correlated with the cell number of stimulator cells used. When DCs were used as stimulator cells maximum T cell proliferation was obtained with 5000–50000 DCs/well on day 3 and 5, but only 3000–5000 DCs/well on day 7. With higher cell numbers of DCs T cell proliferation decreased and when $10^5$ DCs/well were used no T cell proliferation could be measured. It cannot be ruled out that the decrease of T cell proliferation is simply due to the in vitro culture conditions. However, when the same number of CD40-B cells were used, a maximum T cell proliferation could be induced. The T cell proliferative response was essentially dependent on the expression of B7 costimulatory molecules, since blockade of both CD80 (B7-1) and CD86 (B7-2) by CTLA-4Ig significantly decreased T cell proliferation induced by CD40-B cells or DC (open squares). However, when high numbers of CD40-B cells were used, the effect of CTLA-4Ig was clearly diminished and higher concentrations did not further decrease T cell proliferation (data not shown). These data might suggest that CD40-B cells express other molecules able to costimulate. However, they might not play a major role, once the B7/CD28 pathway is present. In contrast, optimal T cell proliferation induced by DCs seems to be completely dependent on B7 costimulation.

Surprisingly, when T cell proliferation of CD4$^+$ CD45RA$^+$ T cells was measured using the same experimental conditions, CD40-B cells induced significantly higher T cell proliferation on days 3 and 5 (FIG. 3, right panel) compared to DCs from the same donor. Only after 7 days of stimulation DCs induced equivalent peak T cell proliferation and this response was induced by 4 fold less stimulator cells (25000 cells/well) compared to CD40-B (100000 cells/well). These data suggest that the two different APCs induce T cell activation and subsequent proliferation with different kinetics with a faster onset by CD40-B cells. In addition, CD4$^+$ CD45RA$^+$ T cell proliferation in this system is highly dependent on costimulation, since blockade with CTLA4-Ig greatly reduced T cell proliferation (open squares).

Since CD8$^+$ T cells are believed to be the major effector T cell we were next interested to identify whether CD40-B and/or DCs could also activate this T cell population. Highly purified CD8$^+$ T cells were stimulated with either increasing numbers of CD40-B or DCs for 3, 5 or 7 days. Interestingly, whereas CD40-B cells induced a profound T cell proliferation of CD8$^+$ T cells DC were significantly less efficient in activating this subpopulation of cells (FIG. 4).

Since both CD40-B cells and DCs were cultured before their APC capacity was assessed, it is difficult to compare these cells with freshly isolated non-activated APCs from the same donor at the same time. We therefore cryopreserved non-activated APCs, CD40-B, and DC cells and compared their capacity to stimulate allogeneic CD4$^+$ CD45RO$^+$ T cells. Only CD40-B cells but not DC cells induced a sufficient T cell proliferative response after cryopreservation (data not shown).

These data suggested that CD40 activated B cells are very efficient allo-APCs comparable to DCs but with different kinetics and cell concentration requirements to obtain equivalent T cell proliferation.

CD40-B cells pulsed with tumor peptide antigen induce peptide specific autologous CD8$^+$ cytotoxic effector T cells. Since we could demonstrate that CD40-B cells are most efficient allo-APCs for CD4$^+$ T cells we were further interested, if these cells could also present antigen to autologous T cells. We were most interested to identify whether these cells could efficiently present MHC class I peptides to CD8$^+$ T cells. Previous data have shown, that human adherent cells [Mukherji, 1995 #95], DCs or activated PBMC [Celis, 1994 #94] could present peptide to autologous T cells in a MHC restricted pattern. Since CD40-B cells expressed very high levels of MHC class I molecules and high levels of adhesion and costimulatory molecules, they were predicted to be very efficient APCs for autologous CD8$^+$ T cells. To test this hypothesis, a model system was applied, using an immunogenic peptide of tyrosinase a melanoma associated tumor antigen [other reference, cloning of tyrosinase]. The tyrosinase 369–377 peptide (SEQ ID NO:1) YMNGTMSQV is known to bind the HLA-A*201 subtype and elicits a T cell response in healthy individuals [Visseren, 1995 #75]. Since it is strongly suggested that this response is a primary T cell mediated immune response, this model system could also answer the question, if CD40-B cells might prime naive human CD8$^+$ T cells in vitro. CD40-B cells were pulsed with the tyrosinase peptide (tyr) and then used to stimulate highly purified CD8$^+$ autologous T cells (>98%) as described in detail in Material in Methods. T cell lines against the tyrosinase peptide (TCL$_{tyr}$) were established and tested for cytotoxicity after 28 days of culture. As seen in FIG. 5A, only HLA-A*201$^+$ CD40-B cells pulsed with Tyr peptide were lysed by TCL$_{tyr}$, whereas HLA-A*201$^+$ CD40-B cells alone were not lysed. In addition HLA-A*201$^+$ PHA blasts, HLA-A*201$^+$ CD40-B cells or HLA-A*201$^+$ CD40-B cells pulsed with irrelevant influenza peptide, which binds HLA-A*201$^+$ were also not lysed (FIG. 5B). Cold target experiments using unlabeled peptide pulsed HLA-A*201$^+$ CD40-B cells confirmed specificity since peptide specific cytotoxicity was abrogated (FIG. 5C). Most important, TCL$_{tyr}$ could kill HLA-A*201$^+$ tyrosinase$^+$ melanoma cells or HLA-A*201$^+$ Tyr peptide pulsed melanoma cells (FIG. 5D). These 15 data suggest that not only DCs (REF) but also CD40-B cells can be used to expand tumor antigen specific MHC class I restricted CD8$^+$ T cells. Similar results were obtained for 5 HLA-A*201$^+$ healthy individuals (Table 1). Only HLA-A*201$^+$ tyrosinase$^+$ melanoma cell lines or HLA-A*201$^+$ Tyr peptide-pulsed CD40-B cells were lysed but none of the control target cells (Table 1).

Continuous activation via CD40 leads to intensive expansion of CD40-B cells with highly efficient APC function. Efficient immunotherapy using professional APCs pulsed with peptides requires multiple vaccinations. Ideally, APCs should be (1) highly efficient in presenting antigen, (2) obtained from small amounts of easy accessible sources such as peripheral blood, (3) obtained in a single procedure, (4) kept in culture in sufficient quantities for subsequent vaccinations, (5) cryopreserved without loosing efficient APC function and (6) expanded to large numbers of cells in vitro. We next addressed these issues for CD40-B cells. While long-term cultures of human B cells repetitively stimulated by CD40 crosslinking have been described, however, the capacity of these long-term cultured cells has not been reported. Moreover, these was typically a problem with outgrowth of T cells. CD40-B cells were cultured for up to 65 days in the CD40L system and these activated B cells could still efficiently present allo-antigen. CD40-B cells were harvested at different time points (days 4, 8, 15, 33, 51 and 65) of culture from the culture and cryopreserved. To compare their APC capacity allogeneic CD4$^+$ T cells were stimulated individually with these CD40-B cells at the same time in a primary MLR. One representative experiment of 3 is depicted in FIG. 6. As expected, unstimulated B cells were very poor APCs (SI) compared to CD40-B cells. There was no significant difference between CD40-B cells cultured for short terms or up to 65 days, indicating that these cells do not change their capacity to present antigen efficiently. However, when costimulation was blocked by the addition of CTLA-4Ig, T cell proliferation to unstimulated B cells and CD40 B cells activated only for short terms was decreased by more than 95%, whereas T cell proliferation induced by CD40-B cells from day 15 was only decreased by 75%. Decrease of T cell proliferation by CTLA-4Ig was further diminished, when CD40-B cells were used which had been activated for more than 30 days. Again, these data indicate, that activated B cells might express other mol ecules able to costimulate and that the expression might increase during continuous activation via CD40. Since this experiments were performed with cryopreserved CD40-B cells we next determined the effect of cryopreservation on APC capacity of these cells. Cryopreserved CD40-B cells (4 days in culture) were compared with non-cryopreserved CD40-B cells in culture for 8 days for their capacity to present alloantigen in a primary MLR with CD4$^+$ T cells. No significant (p>0.5) decrease of T cell proliferation was measured using cryopreserved CD40-B cells (data not shown) suggesting that these cells do not lose APC capacity by cryopreservation.

Since CD40-B cells showed highly efficient APC capacity even after long-term culture, we predicted that these cells should express high levels of adhesion, MHC and costimulatory molecules. To address these issue, we analyzed CD40-B cells for the expression of MHC class I and II, CD54 (ICAM-1) and CD58 (LFA-3) and the costimulatory molecules CD80 (B7-1) and CD86 (B7-2) at weekly intervals during culture. The expression of all molecules increased dramatically during the first days in culture (data not shown) and reached highest expression after 15 days of continuous activation by CD40. After 15 days of culture only CD20$^+$ CD19$^+$ B cells were obtained under optimized culture conditions (FIG. 7). Expression for MHC class I and II increased by 2× fold, CD58, CD80 and CD86 were highly upregulated and the expression of CD54 increased by 2–3× fold at day 15 of culture. Thereafter, CD40-B cells showed high levels of expression throughout the whole culture period, however the expression of MHC class I and costimulatory molecules gradually decreased overtime (FIG. 7). In context with the MLR using blocking CTLA4-Ig these data strongly suggest that other costimulatory molecules must account for the equal capacity of these long-term cultured cells to present allo-antigen.

Next we determined whether under optimized culture conditions (REF) CD40-B cells could be expanded in vitro sufficiently for multiple vaccinations. Pure CD40-B cells were obtained from leukophoresis preparations from healthy donors by direct culture of the mononuclear cell fraction after Ficoll-density centrifugation onto CD40L transfectants in the presence of IL-4 (2 ng/ml) and Cyclosporin A ($5 \times 10^{-7}$M). Total mononuclear cell fractions after Ficoll density centrifugation ranged from $0.81 \times 10^9$ to $3.6 \times 10^9$ cells with 1.8–9.7% CD19$^+$ B cells ($4 \times 10^7$–$2.35 \times 10^8$ cells). After 15 days of culture 92.2–99.8% of cells recovered were CD19$^+$ and the number of CD19$^+$ B cells (CD40-B) dramatically increased by 83–773 fold reaching total CD19$^+$ cell numbers between $19.2$–$133 \times 10^9$ cells (Table 2).

TABLE 2

Expansion (fold increase) of CD19$^+$ B cells in the CD40L system. Fold increase is calculated as described in material and methods. (LP Leukophoresis preparation).

| cell numbers (× 10$^9$) | LP1 | LP2 | LP3 | LP4 | LP5 | LP6 | LP7 |
|---|---|---|---|---|---|---|---|
| day 0 | | | | | | | |
| total number of cells | 1.87 | 3.6 | 3.28 | 2.42 | 3.28 | 2.70 | 0.81 |
| number of CD10$^+$ cells | 0.0785 | 0.191 | 0.059 | 0.235 | 0.082 | 0.081 | 0.04 |
| % CD19$^+$ cells | 4.2 | 5.3 | 1.8 | 9.7 | 2.5 | 3.0 | 4.9 |
| day 15 | | | | | | | |
| number of CD19$^+$ cells | 20.9 | 133 | 45.6 | 19.4 | 19.2 | 33.2 | 7.15 |
| % CD19$^+$ cells | 94.7 | 96.3 | 94 | 97.4 | 92.2 | 98.8 | 99.8 |
| fold increase | 266 | 696 | 773 | 83 | 234 | 410 | 166 |

These cells could be further expanded over the total culture period and reached expansions between 12252 (LP6, day 62) and 98392 (LP2, day 65) fold increase (Table 3).

TABLE 3

Long-term expansion (fold increase) of CD19$^+$B cells in the CD40L system. Fold increase is calculated as described in material and methods. (LP = Leukophoresis preparation; n.d. = not determined)

| fold increase CD19$^+$ | LP2 | LP3 | LP6 |
|---|---|---|---|
| day 0 | 1 | 1 | 1 |
| day 5 | 16 | 21 | 11 |
| day 8 | 95 | 92 | 87 |
| day 12 | 263 | 276 | 167 |
| day 15 | 696 | 773 | 410 |
| day 22 | 1044 | 1546 | 512 |
| day 29 | 1279 | 1695 | 895 |
| day 40 | 3677 | 3365 | 1091 |
| day 48 | 4850 | 3728 | 3425 |
| day 55 | 18862 | 6596 | 4969 |
| day 58 | 36467 | 7695 | 4967 |
| day 62 | 95218 | 16930 | 12252 |
| day 65 | 98392 | 35553 | n.d |

Since we obtained such large quantities of CD40-B cells from leukophoresis preparations we next determined whether we also could generate sufficient numbers of CD40-B cells from peripheral blood. 100 cc of peripheral blood from 5 healthy individuals were ficoll density centrifuged and PBMC cultured following the same optimized culture conditions for 15 days (Table 4). Again, CD40-B cells were obtained with high purity after 15 days of culture (91.7–98.3%) and cell number of CD19$^+$ cells increased dramatically (268–515 fold increase, $4.36$–$6.11 \times 10^8$ cells). These data suggest indeed that CD40-B cells can be obtained from small amounts of peripheral blood in a single procedure, expanded to sufficient quantities for subsequent vaccinations, and cryopreserved without loosing efficient APC function.

TABLE 4

Expansion (fold increase) of CD19+B cells in the CD40L system.
Fold increase is calculated as described in material and methods.
(PBL = Peripheral blood lymphocytes)

| cell numbers (× $10^8$) | PBL1 | PBL2 | PBL3 | PBL4 | PBL5 |
|---|---|---|---|---|---|
| day 0 |  |  |  |  |  |
| total cell number | 0.696 | 0.960 | 0.714 | 0.564 | 0.594 |
| number of CD10+ cells | 0.015 | 0.019 | 0.018 | 0.009 | 0.011 |
| % CD19+ cells | 2.12 | 1.95 | 2.5 | 1.5 | 1.8 |
| day 15 |  |  |  |  |  |
| number of CD19+ cells | 5.38 | 6.11 | 4.49 | 4.36 | 4.52 |
| % CD19+ cells | 91.7 | 98.3 | 96.5 | 98.1 | 95.7 |
| fold increase | 365 | 326 | 268 | 515 | 422 |

Immunosuppressive cytokines reduce APC function of DCs but not CD40-B cells. Another obstacle of adoptive immunotherapy, including vaccination with professional APCs is that immunosuppressive conditions exist in the tumor bearing host (REF). This immune dysfunction has been well documented in tumor patients and tumor cells have been reported to express and release immunosuppressive cytokines including IL-10 and TGFβ. If adoptive immunotherapy such as vaccination with peptide-pulsed APCs should be successful, it is also important to determine if professional APC can still induce efficient T cell stimulation under immunosuppressive conditions. To determine, whether DC or CD40-B cells would lose their capacity to present antigen efficiently when cytokines such as IL-10 or TGFβ are present, we performed allogeneic MLRs using purified CD4+ CD4SRO+ T cells as stimulator cells and DC or CD40-B cells as responder cells in the presence of single cytokines or their combinations. DCs and CD40-B cells were used at a variety of different cell numbers ranging from 1500 cells/well to $10^5$ cells/well and at optimal concentrations are shown here. Allogeneic T cells were used at $10^5$ cells/well. When IL-10, TGFβ1 or TGFβ2 were added throughout the co-culture T cell proliferation induced by DCs was significantly reduced (p=75% decrease) by all three cytokines (FIG. 8A) whereas none of these cytokines had any significant effect on T cell proliferation induced by CD40-B cells (FIG. 8B). The combination of TGFβI and TGFβ2 did not further reduce T cell proliferation induced by DCs, but when TGFβ1 was combined with IL-10 a 85% decrease of T cell proliferation was observed and the combination of IL-10 and TGFβ2 completely blocked proliferation (FIG. 8A). In contrast, when CD40-B cells were studied, the combination of the above cytokines did not lead to any decreased T cell proliferation (FIG. 8B). This data indicate that CD40-B cells and DCs clearly differ in their capacity to present antigen efficiently under immunosuppressive conditions. This effect is partially due to downregulation of costimulatory molecules on DCs but not on CD40-B cells by IL-10 and/or TGFβ (data not shown), however, we have evidence that additional mechanisms might account for this effect.

The invention has been described in detail with reference to preferred embodiments thereof. However, it will be appreciated that those skilled in the art, upon consideration of this disclosure, may make modifications and improvements within the spirit and scope of the invention.

REFERENCES

1. H. J. Armitage, et al., *Nature* 351, 80–82 (1992).
2. J. Banchereau, et al. *Ann. Rev. Immunol.* 12, 881–899 (1994).
3. S. Beissert, S. E. Ulirich, J. Hosoi, R. D. Granstein, *J. Leukocyte Biol.* 58, 234–40 (1995).
4. H. Bernhard, et al., *Cancer Research* 55, 1099–1104 (1995).
5. I. D. Bernstein, et al., *Blood* 79, 1811–1816 (1992).
6. T. Boon, J. C. Cerottini, B. Eynde, P. Bruggen, A. V. Pel, *Ann. Rev. Immunol.* 12, 337–366 (1994).
7. T. Boon, et al. *In Important Advances in Oncology* 1994 V. T. J. DeVita, S. Heilman, S. A. Rosenberg, Eds. (J. B.) Lippincott Company, Philadelphia, 1994) pp. 53–69.
8. V. A. Boussiotis, et al., *Proc. Nati. Acad. Sci.* USA 90, 11059–63 (1993).
9. V. A. Boussiotis, L. M. Nadler, J. L. Strominger, A. E. Goldfeld, *Proc. Nat. Acad. Sci.* USA.91, 7007–7011 (1994).
10. C. Caux, C. Dezutter-Dambuyant, D. Schmitt, J. Banchereau, *Nature* 360, 258–261 (1992).
11. C. Caux, Y.-J. Liu, J. Banchereau, *Immunol. Today* 16, 1–5 (1995).
12. E. Celis, et al., *Proc. Nat. Acad. Sci.* (USA) 91, 2105–9 (1994).
13. C. M. Celluzzi, J. I. Mayordomo, W. J. Storkus, M. I. Lotze, L. D. Falo, *J. Exp. Med.* 163, 283–287 (1996).
14. P. J. Cohen, P. A. Cohen, S. A. Rosenberg, S. I. Katz, J. J. Mule, *Eur. J. Immunol.* 24, 315–319 (1994).
15. R. de Waal Malefyt, et al., *J. Exp. Med.* 174, 915–924 (1991).
16. G. Dranoff, R. C. Mulligan, *Adv. Immunol.* 58, 417–453 (1995).
17. J. Ellis, et al., *Eur. J. Immunol.* 21:2803–2809. (1991).
18. A. H. Enk, S. I. Katz, *J. Immunol.* 149, 92–5 (1992).
19. C. D. Enk, D. Sredni, A. Blauvelt, S. I. Katz, *J. Immunol.* 154, 4851–6 (1995).
20. V. Flamand, et al., *Eur. J. Immunol.* 24:605–610 (1994).
21. V. Flamand, et al., *Eur J. Immunol.* 24:605–610 (1994).
22. A.-C. Fluckiger, P. Garrone, I. Durand, J.-P. Galizzi, J. Banchereau, *J. Exp. Med.* 178, 1473–1481 (1993).
23. G. J. Freeman, et al., *J. Immunol.* 143, 2714–22 (1989).
24. G. J. Freeman, et al., *Science* 262, 909–911 (1993).
25. E. J. Fuchs, P. Matzinger, *Science* 258, 1156–9 (1992).
26. S. Grabbe, S. Beissert, T. Schwarz, R. D. Granstein, *Immunol. Today* 16, 117–121 (1995).
27. D. Hollenbaugh1 et al., *EMBO J.,* 11, 4313–21 (1992).
28. D. Hollenbaugh, H. D. Ochs, H. J. Noelle, J. A. Ledbetter, A. Aruffo, *Immunol Rev.* 138, 23–37 (1994).
29. F. J. Hsu, et al., *Nature Medicine* 2, 52–58 (1996).
30. K. Inaba, J. W. Young, R. M. Steinman, *J. Exp. Med.* 166, 182–194 (1987).
31. K. Inaba, et al., *J. Exp. Med.* 176, 1693–1702 (1992).
32. M. C. Jacob, et al., *Blood,* 75, 1154–1162 (1990).
33. M. K. Jenkins, E. Burrell, J. D. Ashwell, *J. Immunol.* 144, 1585–1590 (1990).
34. J. G. Johnson, M. K. Jenkins, *J. Invest. Dermatol.* 99, 62S-65S (1992).
35. C. H. June, J. A. Ledbetter, P, S. Linsley, C. B. Thompson, *Immunol. Today* 11, 211–6 (1990).
36. C. H. June, J. A. Bluestone, L. M. Nadler, C. B. Thompson, *Immuunol. Today,* 15, 321–31 (1994).
37. R. Khanna, C. A. Jacob, S. R. Burrows, D. J. Moss, *J. Immunol. Methods* 164, 41–9 (1993).
38. A. Lanzavecchia, *Science* 260, 937–943 (1993).
39. C. P. Larsen, S. C. Ritchie, T. C. Pearson, P. S. Linsley, R. P. Lowry, *J. Exp. Med.* 176, 1215–1220 (1992).
40. C. P. Larsen, et al., *J. Immunol.* 152, 5208–19 (1994).
41. O. Lassila, O. Vainio, P. Matzinger, *Nature* 334, 253–5 (1988).

42. D. R. Leach, M. F. Krummel, J. P. Allison, *Science* 271, 1734–1736 (1996).
43. B. L. Levine, et al., *Science* 272, 1939–1943 (1996).
44. J. Limpens, et al., *Immunology* 73, 255–63 (1991).
45. P. S. Linsley, et al., *J. Exp. Med.* 173, 721–730 (1991).
46. S. Luna-Fineman, J. E. Lee, B. S. Wesley, C. Clayberger, A. M. Krensky, *Cancer* 70, 2181–2186 (1992).
47. S. E. Macatonia, R. Lau, S. Patterson, A. J. Pinching, S. C. Knight, *Immunol.* 71, 38–45 (1990).
48. S. E. Macatonia, S. Patterson, S. C. Knight, *Immunol.* 74, 399–406 (1991).
49. A. Mackensen, et al., *Blood* 86, 2699–2707 (1995).
50. P. Matzinger, *J. Immunol. Methods* 145, 185–192 (1991).
51. P. Matzinger, *Ann. Rev. Immunol.* 12, 991–1045 (1994).
52. J. Metlay, E. Pure, H. Steinman, *Advances in Immunology* 47, 45–116 (1989).
53. J. E. Ming, C. Cernetti, R. M. Steinman, A. Granelli-Piperno, *J. Mol. Cell Immunol.* 4, 203–11 (1989).
54. J. E. Ming, R. M. Steinman, A. Granelli-Piperno, *Clin. Exp. Immunol.* 89, 148–53 (1992).
55. B. Mukherji, et al., *Proc. Nat. Acad. Sci* (USA) 92, 8078–82 (1995).
56. T. Nitta, K. Sato, K. Okumura, L. Steinman, *Int. J. Cancer* 49, 545–50 (1991).
57. M. C. Nussenzweig, H. M. Steinman, *J. Exp. Med.* 151, 1196 (1980).
58. P. Paglia, C. Chiodoni, M. Rodolfo, M. P. Colombo, *J. Exp. Med.* 183, 317–322 (1996).
59. M. A. Panzara, E. Gussoni, L. Steinman, J. H. Oksenberq, *Biotechniques* 12, 728–35 (1992).
60. D. Pardoll, *Current Opinion in Oncology* 4, 1124–9 (1992).
61. D. M. Pardoll, *Immunology Today* 14, 310–31(3 (1993).
62. D. M. Pardoll, *Curr. Opin. Immunol* 5, 719–725 (1993).
63. D. M. Pardoll, *Nature* 369, 357 (1994).
64. J. Peguet-Navarro, et al., *Eur. J. Immunol.* 24, 884–91 (1994).
65. L. M. Pinchuk, P. S. Polacino, M. B. Agy, S. J. Klaus, E. A. Clark, *Immunity* 1, 317–325 (1994).
66. E. A. Ranheim, T. J. Kipps, *J. Exp. Med.* 177, 025–935 (1993).
67. J. M. Rivas, S. E. Ulinch, *J. Immunol.* 149, 3865–71 (1992).
68. N. Romani, et al., *J. Exp. Med.* 180, 83–93 (1994).
69. F. Sallusto, A. Lanzavecchia, *J. Exp. Med.* 179, 1109–18 (1994).
70. J. S. Schultze, et al., *Proc. Nat. Acad. Sci.* USA 92, 8200–8204 (1995).
71. R. H. Schwartz, O. L. Mueller', M. K. Jenkins, H. Quill, *Cold Spring Harb. Symp. Quant. Biol.* 54, 605–10 (1989).
72. R. H. Schwartz, *Science* 248, 1349–1356 (1990).
73. R. H. Schwartz, *Cell* 71, 1065–1068 (1992).
74. D. J. Schwartzentruber, M. Stetler-Stevenson, S. A. Hosenberg, S. L. Topatian, *Blood* 82, 1204–1211 (1993).
75. R. M. Steinman, Annual Review of *Immunology* 9, 271–296 (1991).
76. H. M. Steinman, J. W Young, *Current Opinion in Immunology* 3, 361–372 (1991).
77. P. Szabolcs, M. A. Moore, J. W. Young, *J. Immunol.* 154, 5851–5861 (1995).
78. J. G. Tew, G. H. Thorbecke, H. M. Steinman, *J. Reticuloendothel Soc.* 31, 371 (1982).
79. H. Thomas, L. S. Davis, P. E. Lipsky, *J. Immunol.,* 151, 6840–52 (1993).
80. L. F. Thomson, et al., *Tissue Antigens* 35, 9–19 (1990).
81. S. L. Topalian, *Curr. Opin. Immunol.* 6, 741–745 (1994).
82. S. E. Ulirich, *J. Immuno.* 152, 3410–6 (1994).
83. P. Vandenberghe, J. Delabie, M. de Boer, C. DeWolf-Peeters, J. L. Ceuppens, *Int. Immunol.* 5, 317–21 (1993).
84. M. J. W. Visseren, et al., *J. Immunol.,* 154, 3991–3998 (1995).
85. P. B. Volc, et al., *J. Invest. Dermatol.* 91, 162–8 (1988).
86. J. W. Young, R. M. Steinman, *J. Exp. Med.* 171, 1315–32 (1990).
87. J. W. Young, et al., *J. Clin. Invest.* 90, 229–37 (1992).
88. J. W. Young, J. Baggers, S. A. Soergel, *Blood* 81, 2987–97 (1993).
89. J. W. Young, K. Inaba, *J. Exp. Med.* 183, 7–11 (1996).
90. S. Zamvil, L. Steinman, Annual Review of *Immunology* 8, 579–622 (1990).
91. L.-J. Zhou, I. F. Tedder, *J. Immunol.* 154, 3821–3835 (1995).
92. L. Zitvogel, et al., *J. Exp. Med.* 183, 87–97 (1996).

---

What is claimed is:

1. A method of promoting B cell proliferation and activation which comprises:
   (a) culturing B cells in vitro in the presence of (1) an effective amount of a CD40 ligand to activate the B oells thereby obtaining activated B cells, (2) a lymphocyte proliferating cytokine, and (3) an immunosuppressive agent, wherein said immunosuppressive agent is cyclosporin A;
   (b) wherein said activated B cells are cultured under conditions that support B cell growth for a period of at least 8 days.

2. The method of claim 1, wherein the lymphocyte proliferating cytokine is IL-4.

3. The method of claim 2, wherein the resultant activated B cells are purified and cryofrozen.

4. The method of claim 2, wherein the activated B cells are grown for at least 14 days.

5. The method of claim 4, wherein the activated B cells are grown for at least 2 months.

6. The method of claim 2, wherein the activated B cells are grown for at least two months.

7. The method of claim 6, wherein said activated B cells are at least 99% pure.

8. The method of claim 6, wherein the B cells cultured in step (a) are obtained from peripheral blood.

9. The method of claim 8, wherein the B cells obtained from peripheral blood are peripheral blood mononuclear cells.

10. The method of claim 7, wherein the B cells cultured in step (a) are obtained from peripheral blood.

11. The method of claim 10, wherein the B cells are peripheral blood mononuclear cells.

* * * * *